United States Patent [19]

Kuroda et al.

[11] Patent Number: 4,957,837

[45] Date of Patent: Sep. 18, 1990

[54] PHOTOSENSITIVE MEMBER FOR ELECTROPHOTOGRAPHY CONTAINING HYDRAZONE IN CHARGE TRANSPORT LAYER

[75] Inventors: Masami Kuroda; Youichi Nakamura; Noboru Furusho, all of Kanagawa, Japan

[73] Assignee: Fuji Electric Co., Ltd., Kanagawa, Japan

[21] Appl. No.: 257,260

[22] Filed: Oct. 13, 1988

[30] Foreign Application Priority Data

| Oct. 15, 1987 | [JP] | Japan | 62-260531 |
| Oct. 20, 1987 | [JP] | Japan | 62-265112 |
| Oct. 20, 1987 | [JP] | Japan | 62-265113 |
| Oct. 21, 1987 | [JP] | Japan | 62-265751 |
| Oct. 21, 1987 | [JP] | Japan | 62-265752 |

[51] Int. Cl.$^5$ ............................................. G03G 5/06
[52] U.S. Cl. ............................................................ 430/59
[58] Field of Search ..................................... 430/58, 59

[56] References Cited

U.S. PATENT DOCUMENTS

| 3,484,237 | 12/1969 | Shattuck et al. | 430/56 |
| 4,278,747 | 7/1981 | Murayama et al. | 430/82 |
| 4,367,273 | 1/1983 | Murayama et al. | 430/56 |
| 4,415,640 | 11/1983 | Goto et al. | |
| 4,568,623 | 2/1986 | Makino et al. | |
| 4,606,986 | 8/1986 | Yanus et al. | |
| 4,624,904 | 11/1986 | Kazmaier et al. | |
| 4,666,809 | 5/1987 | Matsumoto et al. | |
| 4,677,045 | 6/1987 | Champ et al. | |
| 4,702,983 | 10/1987 | Haino et al. | |
| 4,731,315 | 3/1988 | Horie et al. | |
| 4,808,503 | 2/1989 | Yamada et al. | |

FOREIGN PATENT DOCUMENTS

| 131140 | 1/1985 | European Pat. Off. |
| 3019909 | 11/1980 | Fed. Rep. of Germany |
| 3141306 | 6/1982 | Fed. Rep. of Germany |
| 3139524 | 8/1982 | Fed. Rep. of Germany |
| 3203621 | 9/1982 | Fed. Rep. of Germany |
| 3303830 | 8/1983 | Fed. Rep. of Germany |
| 4710785 | 5/1972 | Japan |
| 4737543 | 12/1972 | Japan |
| 4866444 | 9/1973 | Japan |
| 5039952 | 4/1975 | Japan |
| 50455 | 3/1984 | Japan |
| 6093443 | 5/1985 | Japan |
| 264055 | 11/1987 | Japan |

Primary Examiner—J. David Welsh
Attorney, Agent, or Firm—Spencer & Frank

[57] ABSTRACT

A photosensitive member for electrophotography has a photosensitive layer provided on a conductive layer. The photosensitive layeer contains a hydrazone compound represented by the following general formula (I):

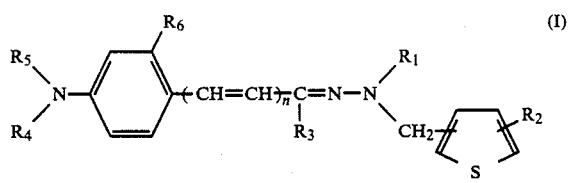

wherein $R_1$ stands for an aryl group which may have a substituent(s); each of $R_2$, $R_3$, $R_4$, $R_5$ and $R_6$ stands for a hydrogen atom, a halogen atom, an alkyl group, an alkoxy group, a hydroxy group, a nitro group, an allyl group, an aryl group which may have a substituent(s), or an aralkyl group; and n stands for an integer of 0 to 1.

18 Claims, 1 Drawing Sheet

PHOTOSENSITIVE MEMBER FOR ELECTROPHOTOGRAPHY CONTAINING HYDRAZONE IN CHARGE TRANSPORT LAYER

BACKGROUND OF THE INVENTION

1. Field of the Invention

The present invention relates to a photosensitive member for electrophotography, and particularly to a photosensitive member for electrophotography which contains a novel hydrazone compound in the photosensitive layer thereof formed on an electroconductive substrate.

2. Description of the Prior Art

Photosensitive materials which have heretofore been used in photosensitive members for electrophotography (hereinafter also referred to as "photosensitive members") include inorganic photoconductive substances such as selenium and selenium alloys, dispersions of inorganic photoconductive substances such as zinc oxide and cadmium sulfide in resin binders, organic polymeric photoconductive substances such as poly-N-vinylcarbazolic and polyvinylanthracene, organic photoconductive substances such as phthalocyanine compounds and bisazo compounds, and dispersions of such organic polymeric photoconductive substances in resin binders.

Photosensitive members are required to have the capabilities of maintaining a surface electric charge in the dark, of generating an electric charge upon receiving light, and of transporting an electric charge upon receiving light. They are classified into two types of photosensitive members, namely the so-called monolayer type photosensitive members, and the so-called laminate type photosensitive members. The former comprises a single layer having all of the above-mentioned functions, and the latter comprises functionally distinguishable laminated layers, one of which contributes mainly to the generation of electric charge, and another of which contributes to the retention of surface electric charge in the dark and electric charge transportation upon receiving light. In an electrophotographic method using a photosensitive member of the kind as mentioned above, for example, the Carlson's system is applied to image formation. The image formation according to this system comprises the steps of subjecting a photosensitive member in the dark to corona discharge to charge the member, illuminating the surface of the charged photosensitive member with imagewise light from a manuscript or copy bearing, e.g., letters and/or pictures to form a latent electrostatic image, developing the formed latent electrostatic image with a toner, and transferring the developed toner image to a support such as a paper sheet to fix the toner image on the support. After the toner image transfer, the photosensitive member is subjected to the steps of removal of the electric charge, removal of the remaining toner (cleaning), neutralization of the residual charge with light (erasion), and so on to be ready for reuse.

Photosensitive members for electrophotography in which use is made of at least one organic material have recently been put into practical use due to the advantageous features of the organic materials such as flexibility, thermal stability, and/or a film forming capacity. They include a photosensitive member comprising poly-N-vinylcarbazole and 2,4,7-trinitrofluoren-9-one (disclosed in U.S. Pat. No. 3,484,237), a photosensitive member using an organic pigment as the main component (disclosed in Japanese Patent Laid-Open No. 37,543/1972), and a photosensitive member using as the main component a eutectic complex composed of a dye and a resin (disclosed in Japanese Patent Laid-Open No. 10,785/1972). A number of novel hydrazone compounds have also been put into practical use for photosensitive members.

Although organic materials have a number of advantageous features mentioned above with which inorganic materials are not endowed, however, the fact is that there have been obtained no organic materials fully satisfying all the characteristics required of a material to be used in photosensitive members for electrophotography at the present. Particular problems for known in organic materials have been photosensitivity and characteristics in continuous repeated use.

SUMMARY OF THE INVENTION

An object of the present invention is to provide a photosensitive member for electrophotography to be used in copying apparatuses and printers which has a high photosensitivity and excellent characteristics in repeated use, through the use, in the photosensitive layer, of novel organic materials not as a charge transporting substance.

In the first aspect of the present invention, a photosensitive member for electrophotography comprises:

a photosensitive layer containing of at least one hydrazone compound represented by the following general formula (I):

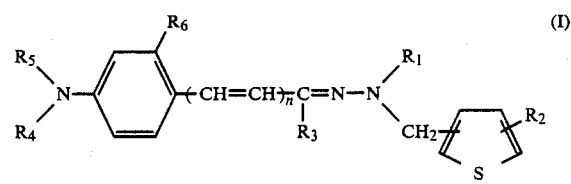

wherein $R_1$ stands for an aryl group which may have at least one substituent; each of $R_2$, $R_3$, $R_4$, $R_5$ and $R_6$ stands for a hydrogen atom, a halogen atom, an alkyl group, an alkoxy group, a hydroxy group, a nitro group, an allyl group, an aryl group which may have at least one substituent, or an aralkyl group; and n stands for an integer of 0 or 1.

Here, the photosensitive layer may comprise a dispersion of a charge generating substance and a charge transporting substance in a binder resin, and the charge transporting substance may be a compound selected from hydrazone compounds represented by the general formula (I).

The photosensitive layer may comprise a laminate of a charge transporting layer mainly composed of a charge transporting substance and a charge generating layer, and the charge transporting substance may be a compound selected from hydrazone compounds represented by the general formula (I).

In the second aspect of the present invention, a photosensitive member for electrophotography comprises: a photosensitive layer containing at least one hydrazone compound represented by the following general formula (II):

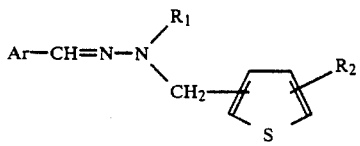

(II)

wherein $R_1$ stands for an aryl group which may have at least one substituent; $R_2$ stands for a hydrogen atom, a halogen atom, an alkyl group, an aryl group, or a nitro group; and Ar stands for a condensed-ring polycyclic aromatic hydrocarbon group.

Here, the photosensitive layer may comprise a dispersion of a charge generating substance and a charge transporting substance in a binder resin, and the charge transporting substance may be a compound selected from hydrazone compounds represented by the general formula (II).

The photosensitive layer may comprise a laminate of a charge transporting layer mainly composed of a charge transporting substance and a charge generating layer, and the charge transporting substance may be a compound selected from hydrazone compounds represented by the general formula (II).

In the third aspect of the present invention, a photosensitive member for electrophotography comprises:

a photosensitive layer containing at least one hydrazone compound represented by the following general formula (III):

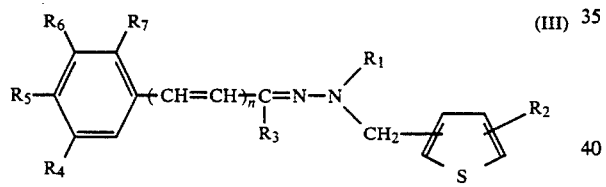

(III)

wherein $R_1$ stands for an aryl group which may have at least one substituent; each of $R_2$, $R_3$, $R_4$, $R_5$, $R_6$ and $R_7$ stands for a hydrogen atom, a halogen atom, an alkyl group, an alkoxy group, a phenoxy group, a nitro group, a hydroxy group, an aryl group, or a styryl group; and n stands for an integer of 0 or 1.

Here, the photosensitive layer may comprise a dispersion of a charge generating substance and a charge transporting substance in a binder resin, and the charge transporting substance may be a compound selected from hydrazone compounds represented by the general formula (III).

The photosensitive layer may comprise a laminate of a charge transporting layer mainly composed of a charge transporting substance and a charge generating layer, where the charge transporting substance may be a compound selected from hydrazone compounds represented by the general formula (III).

In the fourth aspect of the present invention, a photosensitive member for electrophotography comprises:

a photosensitive layer containing at least one hydrazone compound represented by the following general formula (IV):

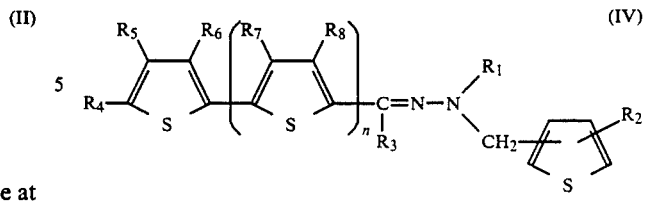

(IV)

wherein $R_1$ stands for an aryl group which may have at least one substituent; each of $R_2$, $R_3$, $R_4$, $R_5$, $R_6$, $R_7$ and $R_8$ stands for a hydrogen atom, a halogen atom, an alkoxy group, an alkyl group, a nitro group, a hydroxy group, an aryl group, or an amino group which may have at least one substituent; and n stands for an integer of 1, 2, 3 or 4.

Here, the photosensitive layer may comprise a dispersion of a charge generating substance and a charge transporting substance in a binder resin, where the charge transporting substance may be a compound selected from hydrazone compounds represented by the general formula (IV).

Alternatively, the photosensitive layer may comprise a laminate of a charge transporting layer mainly composed of a charge transporting substance and a charge generating layer, where the charge transporting substance may be a compound selected from hydrazone compounds represented by the general formula (IV).

In the fifth aspect of the present invention, a photosensitive member for electrophotography comprises:

a photosensitive layer containing at least one hydrazone compound represented by the following general formula (V):

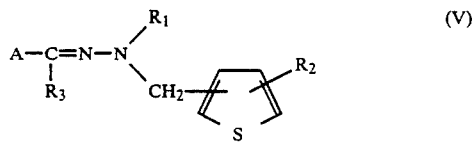

(V)

wherein $R_1$ stands for an aryl group which may have at least one substituent; each of $R_2$ and $R_3$ stands for a hydrogen atom, a halogen atom, an alkyl group, an alkoxy group, an aryl group or a nitro group; and Ar stands for a heterocyclic group which may have at least one substituent.

Here, the photosensitive layer may comprise a dispersion of a charge generating substance and a charge transporting substance in a binder resin, where the charge transporting substance may be a compound selected from hydrazone compounds represented by the general formula (V).

Alternatively, the photosensitive layer may comprise a laminate of a charge transporting layer mainly composed of a charge transporting substance and a charge generating layer, where the charge transporting substance may be a compound selected from hydrazone compounds represented by the general formula (V).

In the sixth aspect of the present invention, a photosensitive member for electrophotography comprises:

a photosensitive layer containing at least one hydrazone compound represented by the following general formula (VI) or (VII):

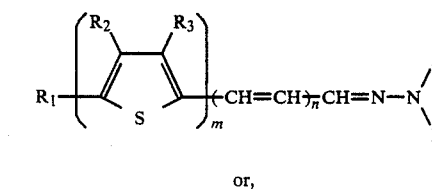

(VI)

or,

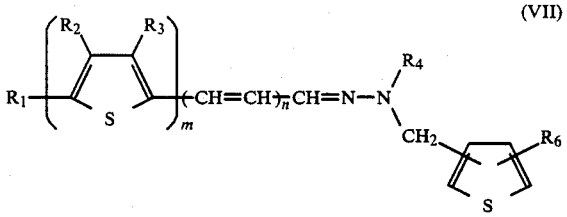

(VII)

wherein each of $R_1$, $R_2$, $R_3$ and $R_6$ stands for a hydrogen atom, a halogen atom, an alkyl group, an alkoxy group, a hydroxy group, an allyl group, a nitro group, an aryl group which may have at least one substituent, or an amino group; each of $R_4$ and $R_5$ stands for an aryl group which may have at least one substituent; n stands for an integer of 0 or 1; and m stands for an integer of 2 to 5.

Here, the photosensitive layer may comprise a dispersion of a charge generating substance and a charge transporting substance in a binder resin, where the charge transporting substance may be a compound selected from hydrazone compounds represented by the general formula (VI) or (VII).

Alternatively, the photosensitive layer may comprise a laminate of a charge transporting layer mainly composed of a charge transporting substance and a charge generating layer, where the charge transporting substance may be a compound selected from hydrazone compounds represented by the general formula (VI) or (VII).

The above and other objects, effects, features and advantages of the present invention will become more apparent from the following description of embodiments thereof taken in conjunction with the accompanying drawings.

DETAILED DESCRIPTION OF PREFERRED EMBODIMENTS

Figure 1:
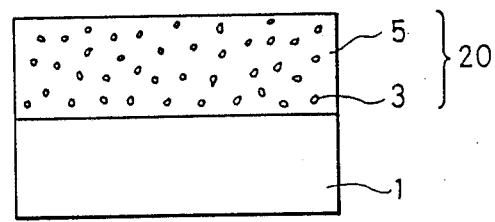
FIGS. 1 to 3 are schematic cross-sectional views of photosensitive members according to the present invention.
Figure 2:
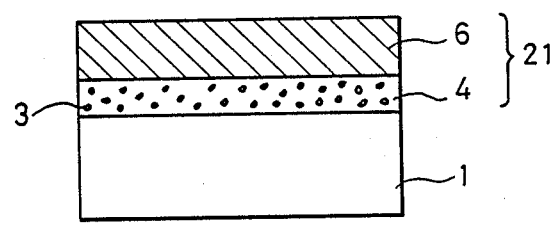
Figure 3:
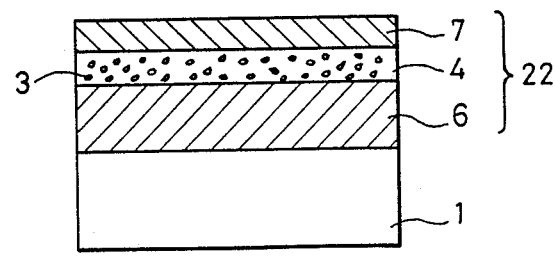

The photosensitive member according to the present invention which contains a hydrazone compound in the photosensitive layer thereof may be in the form of any one of the structures of FIGS. 1, 2 and 3, depending on the way of application of the hydrazone compound thereto.

FIG. 1 shows a photosensitive member comprising an electroconductive substrate 1, and a photosensitive layer 20 provided thereon and which contains charge generating substance 3 dispersed in a matrix 5 which is composed of a hydrazone compound, as a charge transporting substance, and a resin binder. This structure is referred to as a monolayer type photosensitive member.

FIG. 2 shows a photosensitive member comprising an electroconductive substrate 1, and a photosensitive layer 21 provided thereon composed of laminated layers, the lower one of which is a charge generating layer 4 containing a charge generating substance 3 as the main component, and the upper one of which is a charge transporting layer 6 containing a hydrazone compound as a charge transporting substance. This structure is referred to as a laminate type photosensitive member which is usually used according to the negative charge mode.

FIG. 3 shows a photosensitive member having a layer structure in reverse to that of FIG. 2 and comprising an electroconductive substrate 1, and a photosensitive layer 22 provided thereon composed of laminated layers, the lower one of which is a charge transporting layer 6 containing a hydrazone compound as a charge transporting substance, and the middle one of which is a charge generating layer 4 containing a charge generating substance 3 as the main component. This photosensitive member is usually used according to the positive charge mode. In this case, a covering layer 7 may generally be further provided as shown in FIG. 3 to protect the charge generating layer 4.

Thus, in the case of laminate type photosensitive members, the charge mode therefor differs depending on the layer structure. The reason for this is that, even where any photosensitive member with the layer structure as shown in FIG. 2 is to be used in the positive charge mode, no charge transporting substances adaptable to the positive charge mode have been found yet. Accordingly, when any laminate type photosensitive member is to be used in the positive charge mode, the photosensitive member is required of the layer structure as shown in FIG. 3 at present.

A photosensitive member as shown in FIG. 1 can be produced by dispersing a charge generating substance in a solution of a charge transporting substance and a resin binder and applying the resulting dispersion on an electroconductive substrate.

A photosensitive member as shown in FIG. 2 can be prepared by depositing a charge generating substance on an electroconductive substrate by means of vacuum evaporation or applying and drying a dispersion of a particulate charge generating substance in a solvent and/or a resin binder on an electroconductive substrate, followed by applying a solution of a charge transporting substance and a resin binder on the resulting layer and drying.

A photosensitive member as shown in FIG. 3 can be prepared by applying and drying a solution of a charge transporting substance and a resin binder on an electroconductive substrate, and depositing a charge generating substance on the resulting coating layer by means of vacuum evaporation or coating and drying a dispersion of a particulate charge generating substance in a solvent and/or a resin binder on the charge transporting layer, followed by the formation of a covering layer.

The electroconductive substrate 1 serves as an electrode for the photosensitive member and as a support for at least one layer formed thereon. The electroconductive substrate may be in the form of a cylinder, a plate or a film, and may be made of a metallic material such as aluminum, stainless steel or nickel, or other material having an electroconductive surface, such as a treated glass or a treated resin.

The charge generating layer 4 formed by the application of a dispersion of a particulate charge generating substance 3 in a resin binder or by deposition of a charge generating substance by means of vacuum evaporation, or the like technique as described above, generates an electric charge upon receiving light. It is important that the charge generating layer 4 be high not only in charge generating efficiency but also in capability of injecting the generated electric charge into the charge transporting layer 6 and any covering layer 7. This capability is desirably as little dependent upon the electric field as possible and is high even in low intensity electric fields. Usable charge generating substances include phthalocyanine compounds such as metal-free phthalocyanine and titanyl phtholocyanine; various azo, quinone and indigo pigments; dyes such as cyanine, squalilium, azulenium and pyrylium compounds; and selenium and selenium compounds. Among those, a suitable compound can be chosen depending on the wavelength range of the light source used for the image formation. The thickness of the charge generating layer is determined by the extinction coefficient of the charge generating substance to be used therein in view of the layer's function of generating an electric charge, but is generally 5 μm or smaller, preferably 1 μm or smaller. It also is possible to form a charge generating layer using a charge generating substance as a main component in admixture with a charge transporting substance and so on. Resin binders usable in the charge generating layer include polycarbonates, polyesters, polyamides, polyurethanes, epoxy resins, silicone resins, and methacrylate homopolymer and copolymers, which may be used either alone or in appropriate combination.

The charge transporting layer 6 is a coating containing a hydrazone compound as an organic charge transporting substance in a resin binder. The charge transporting layer serves as an insulator layer in the dark so as to retain the electric charge of the photosensitive member, and fulfills the function of transporting an electric charge injected from the charge generating layer upon receiving light. Resin binders usable in the charge transporting layer include polycarbonates, polyesters, polyamides, polyurethanes, epoxy resins, silicone resins, and methacrylate homopolymer and copolymers.

The covering layer 7 serves the function of receiving and retaining an electric charge generated by corona discharge in the dark and the capability of transmitting light to which the charge generating layer should respond. It is necessary that the covering layer transmits light upon exposure of the photosensitive member and allows the light to reach the charge generating layer, and then undergoes the injection of an electric charge generated in the charge generating layer to neutralize and erase a surface electric charge. Materials usable in the covering layer include organic insulating, film-forming materials such as polyesters and polyamides. Such organic materials may also be mixed with an inorganic material such as a glass, resin or $SiO_2$, or an electric resistance-lowering material such as a metal or a metal oxide. Materials usable in the covering layer are not limited to organic insulating, film-forming materials, and further include inorganic materials such as $SiO_2$, metals, and metal oxides, which may be formed into a covering layer by appropriate application methods such as vacuum evaporation and deposition, or sputtering. From the viewpoint of the aforementioned description, it is desirable that the material to be used in the covering layer be as transparent as possible in the wavelength range wherein the charge generating substance attains maximum light absorption.

Although the thickness of the covering layer depends on the composition thereof, it can be arbitrarily set in so far as it does not produce any adverse effects including an increase in the residual potential in continuous repeated use.

The hydrazone compound to be used in the present invention can be synthesized by a customary method. Specifically, a carbonyl compound such as an aldehyde or a ketone is condensed with a hydrazine compound in a suitable solvent such as an alcohol in the presence of a small amount of an acid as a condensation agent if necessary to synthesize the hydrazone compound.

A carbonyl compound of the formula:

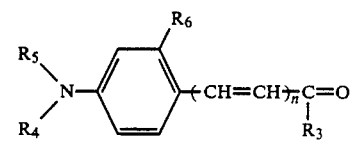

is condensed with a hydrazine compound of the formula:

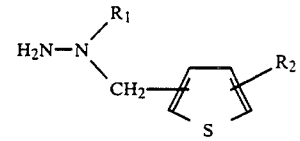

in an alcohol such as ethanol in the presence of a small amount of a catalyst such as hydrochloric acid if necessary evolving $H_2O$, according to the following reaction formula:

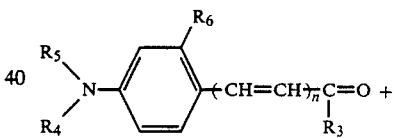

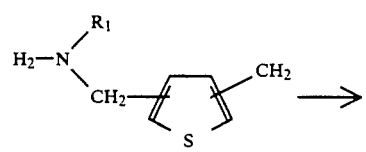

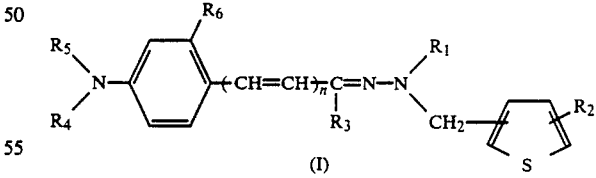

(I)

to synthesize a hydrazone compound represented by the above-mentioned general formula (I). In the general formula (I), $R_1$ stands for an aryl group which may have a substituent(s); each of $R_2$, $R_3$, $R_4$, $R_5$ and $R_6$, stands for a hydrogen atom, a halogen atom, an allyl group, an alkoxy group, a hydroxy group, a nitro group, an allyl group an aryl group which may have a substituent(s), or an aralkyl group; and n stands for an integer of 0 or 1.

Specific examples of the hydrazones compound of general formula (I) prepared in the above-mentioned manner are as follows:

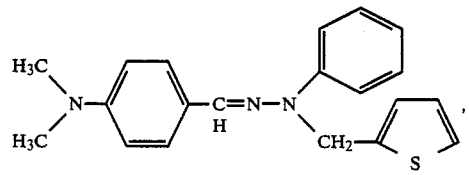
compound I-1
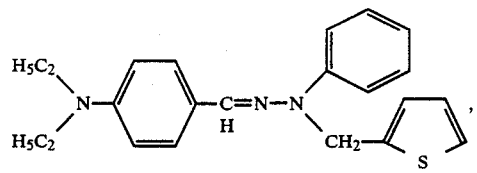
compound I-2
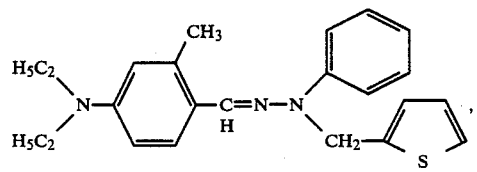
compound I-3
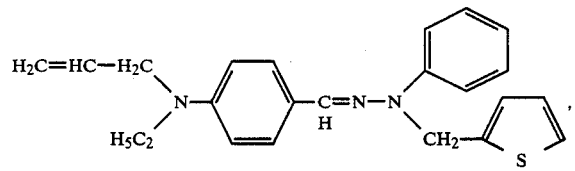
compound I-4
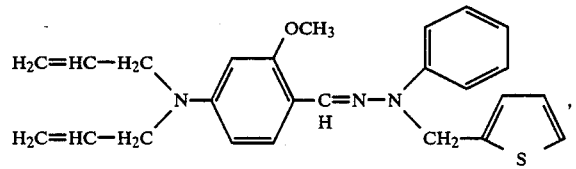
compound I-5
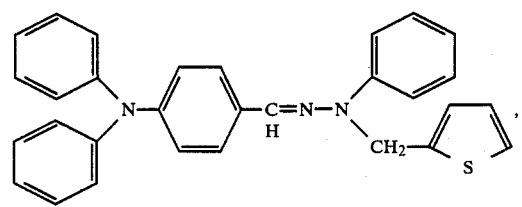
compound I-6
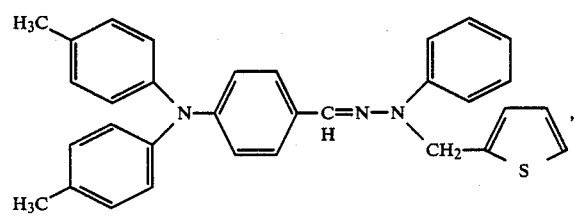
compound I-7
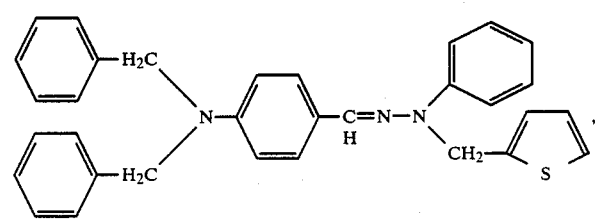
compound I-8 compound I-9
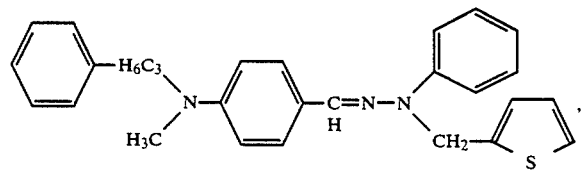
compound I-10
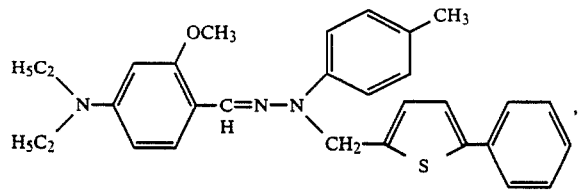
compound I-11
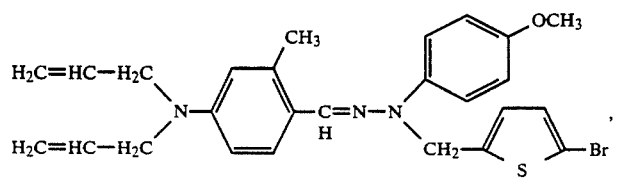
compound I-12
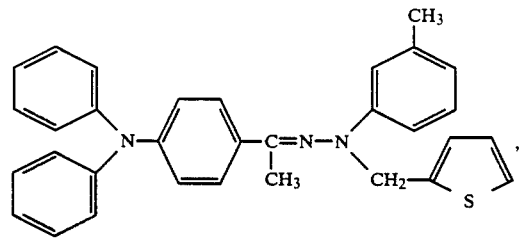
compound I-13
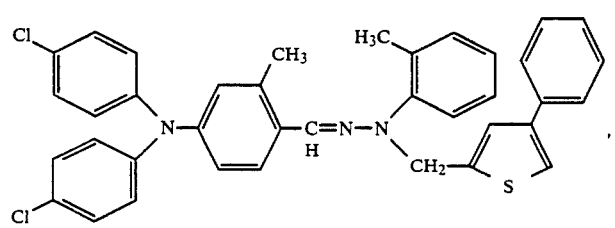
compound I-14
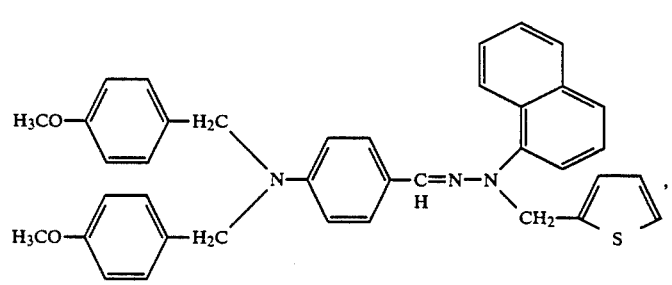
compound I-15
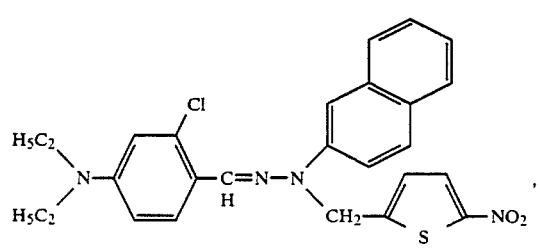

-continued
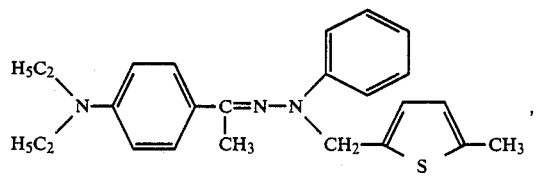
compound I-16
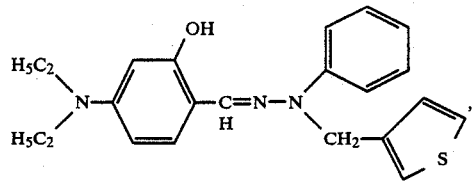
compound I-17
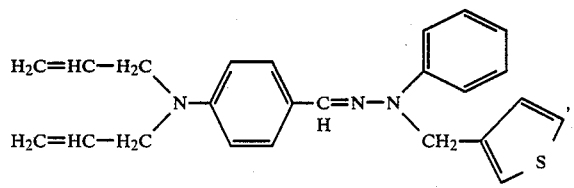
compound I-18
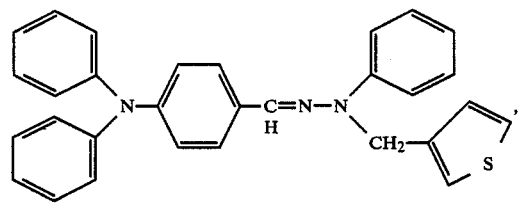
compound I-19
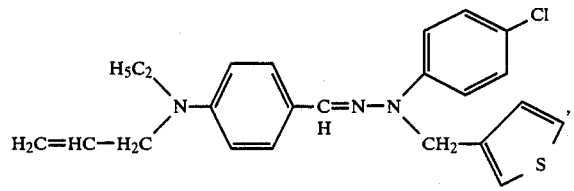
compound I-20
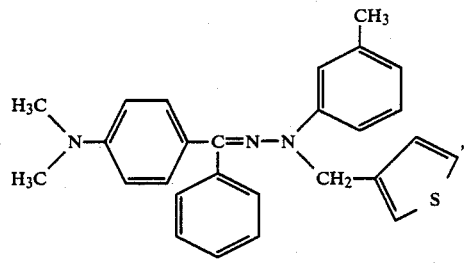
compound I-21
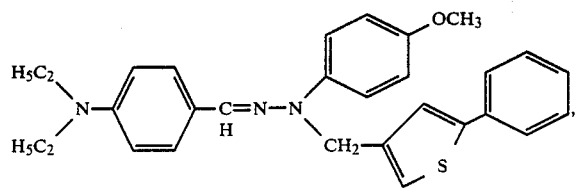
compound I-22 compound I-23
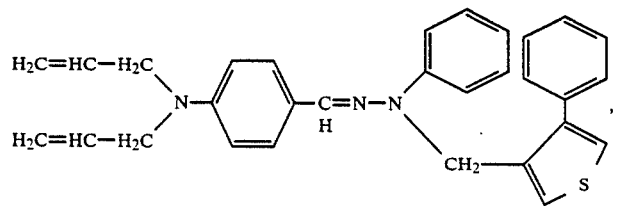
compound I-24
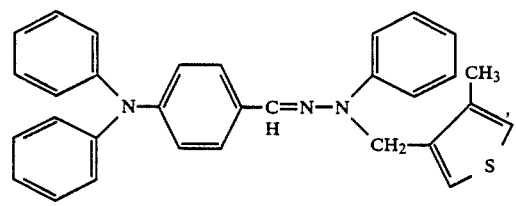
compound I-25
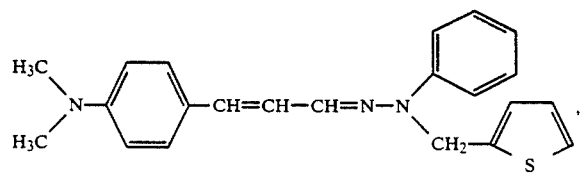
compound I-26
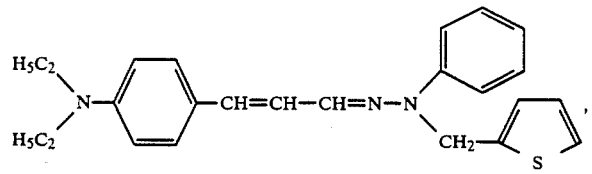
compound I-27
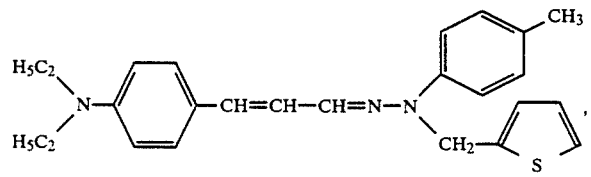
compound I-28
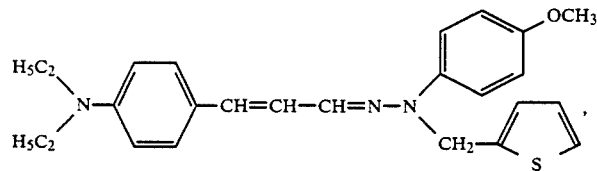
compound I-29
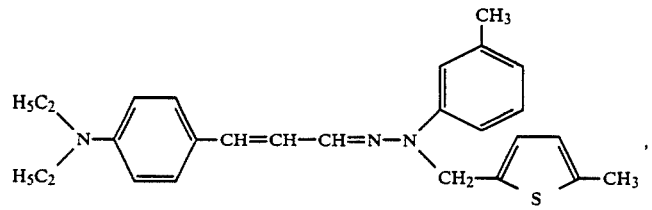
compound I-30
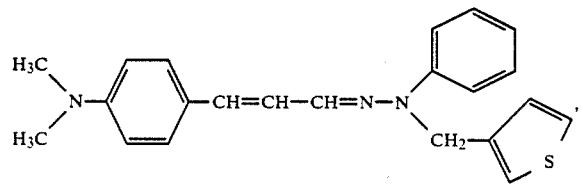

-continued

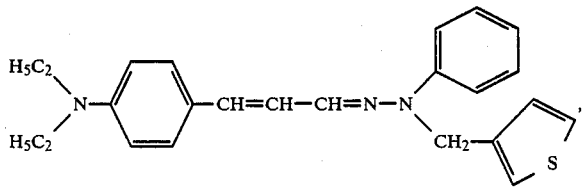

compound I-31 and

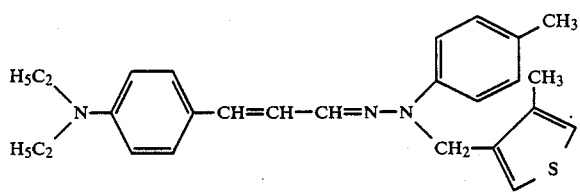

compound I-32

The Examples of the present invention will be explained.

EXAMPLE I-1

50 parts by weight of metal-free phthalocyanine (manufactured by Tokyo Kasei Co., Ltd.) pulverized in a ball mill for 150 hours and 100 parts by weight of the hydrazone compound No. I-1 mentioned above were kneaded together with 100 parts by weight of a polyester resin (Vylon 200 (trademark), manufactured by Toyobo Co., Ltd.) and tetrahydrofuran (THF) as a solvent with a mixer for 3 hours to prepare a coating liquid. The coating liquid was applied on an aluminum-deposited polyester film (Al-PET) as an electroconductive substrate by means of the wire bar technique to form a photosensitive layer having a dry thickness of 15 μm. Thus, a photosensitive member with the structure shown in FIG. 1 was produced.

EXAMPLE I-2

Metal-free α-phthalocyanine as a starting material was pulverized for 20 minutes into a fine powder with a pulverizer, specifically a LIMMAC (linear induction motor mixing and crushing manufactured by Fuji Electric Co., Ltd.) wherein a non-magnetic can containing the metal-free α-phthalocyanine and Teflon pieces as small acting pieces was placed between two linear motors facing each other. The sample of 1 part by weight of the fine powder thus prepared was dispersed in 50 parts by weight of DMF (N,N-dimethylformamide) as a solvent by means of an ultrasonic dispersion treatment. Thereafter, the sample was separated from the DMF by filtration and dried to complete the treatment of metal-free phthalocyanine.

A solution of 100 parts by weight of the hydrazone compound No. I-2 mentioned above in 700 parts by weight of tetrahydrofuran (THF) was mixed with a solution of 100 parts by weight of polymethyl methacrylate (PMMA, manufactured by Tokyo Kasei Co., Ltd.) in 700 parts by weight of toluene to prepare a coating liquid. The coating liquid was applied on an aluminum-deposited polyester film substrate by the wire bar technique to form a charge transporting layer having a dry thickness of 15 μm. 50 parts by weight of metal-free phthalocyanine treated in the above-mentioned manner, 50 parts by weight of a polyester resin (Vylon 200), and 50 parts by weight of PMMA were kneaded with a mixer for 3 hours together with THF as a solvent to prepare a coating liquid, which was then applied on the charge transporting layer by the wire bar technique to form a charge generating layer having a dry thickness of 1 μm. Thus, a photosensitive member with a structure corresponding to that shown in FIG. 3 was produced. No covering layer was provided since the present invention is not directly concerned with a covering layer.

EXAMPLE I-3

A photosensitive member was produced by forming a photosensitive layer in substantially the same manner as in example I-1 except that 50 parts by weight of metal-free phthalocyanine, 100 parts by weight of the hydrazone compound No. I-3 mentioned above, 50 parts by weight of a polyester resin (Vylon 200), and 50 parts by weight of PMMA were used in place of the composition of the photosensitive layer of Example I-1.

EXAMPLE I-4

A photosensitive member was produce by forming a photosensitive layer in substantially the same manner as in Example I-3 except that Chlorodiane Blue which is a bisazo pigment disclosed in, for example, Japanese Patent Laid-Open No. 37,543/1972 was used instead of metal-free phthalocyanine.

The electrophotographic characteristics of the four photosensitive members thus produced were measured by utilizing an electrostatic recording paper testing apparatus (Kawaguchi Denki Model SP-428).

The surface potential $V_s$ (volts) of each photosensitive member is an initial surface potential which was measured when the surface of the photosensitive member was positively charged in the dark by corona discharge at +6.0 kV for 10 seconds. After the discontinuance of the corona discharge, the member was allowed to stand in the dark for 2 seconds, after which the surface potential $V_d$ (volts) of the member was measured. Subsequently, the surface of the photosensitive member was irradiated with white light at an illuminance of 2 luxes and the time (seconds) required for the irradiation to decrease the surface potential of the member to half of $V_d$ was measured. From that time and the illuminance the half decay exposure amount $E_{\frac{1}{2}}$ (lux·sec) was calculated. Also, the surface potential of the member after 10 seconds of irradiation thereof with white light at an illuminance of 2 luxes was measured as a residual potential $V_r$ (volts). When a phthalocyanine compound was used as the charge generating substance, a high sensitivity could be expected for light with longer wavelengths. Hence, the electrophotographic characteristics thereof were also measured by using a monochromatic light with a wavelength of 780 nm. Specifically, $V_s$ and $V_d$ of each member were measured in the same manner as described above, and the half decay exposure amount ($\mu J/cm^2$) was found by irradiation of the member surface with a monochromatic light (wavelength: 780 nm) of 1 $\mu W$ instead of white light, while the residual potential $V_r$ (volts) was measured after seconds of irradiation of the member surface with the above-mentioned light. The results of the measurements are shown in Table 1.

TABLE 1

| Example No. | White Light | | | Light with Wavelength of 780 nm | | |
|---|---|---|---|---|---|---|
| | $V_s$ (volts) | $V_r$ (volts) | $E_{\frac{1}{2}}$ (lux · sec) | $V_s$ (volts) | $V_r$ (volts) | $E_{\frac{1}{2}}$ ($\mu J/cm^2$) |
| I-1 | 650 | 80 | 5.2 | 670 | 70 | 4.9 |
| I-2 | 700 | 80 | 5.0 | 730 | 60 | 5.1 |
| I-3 | 720 | 100 | 5.8 | 710 | 70 | 5.3 |
| I-4 | 680 | 60 | 4.0 | — | — | — |

As can be seen in Table 1, the photosensitive members of Examples I-1, I-2, I-3 and I-4 were not substantially different therebetween in the half decay exposure amounts and the residual potentials, and showed good surface potential characteristics. The photosensitive members of Examples I-1, I-2 and I-3, using a phthalocyanine compound as the charge generating substance, also showed excellent electrophotographic characteristics for light with the long wavelength of 780 nm.

EXAMPLE I-5

Selenium was deposited on an aluminum plate having a thickness of 500 $\mu m$ by means of vacuum evaporation to form a charge generating layer having a thickness of 1.5 $\mu m$. A solution of 100 parts by weight of the hydrazone compound No. I-4 mentioned above in 700 parts by weight of tetrahydrofuran (THF) was mixed with a solution of 100 parts by weight of polymethyl methacrylate (PMMA, manufactured by Tokyo Kasei Co., Ltd.) in 700 parts by weight of toluene to prepare a coating liquid, which was then applied on the charge generating layer by the wire bar technique to form a charge transporting layer having a dry thickness of 20 $\mu m$. Thus, a photosensitive member with the structure shown in FIG. 2 was produced. This photosensitive member was charged by corona discharge at $-6.0$ kV for 0.2 second and examined with respect to electrophotographic characteristics. Good results were obtained, namely $V_s = -700$ V, $V_r = -600$ V and $E_{\frac{1}{2}} = 4.2$ lux·sec.

EXAMPLE I-6

50 parts by weight of metal-free phthalocyanine treated in the same manner as in Example I-1, 50 parts by weight of a polyester resin (Vylon 200), and 50 parts by weight of PMMA were kneaded together with THF as a solvent with a mixer for 3 hours to prepare a coating liquid, which was then applied on an aluminum support to form a charge generating layer having a thickness of about 1 $\mu m$. Subsequently, 100 parts by weight of the hydrazone compound No. I-5 mentioned above, 100 parts by weight of a polycarbonate resin (Panlite L-1250, manufactured by Teijin Kasei Co., Ltd.), and 0.1 part by weight of a silicone oil were mixed with 700 parts by weight of THF and 700 parts by weight of toluene to prepare a coating liquid, which was then applied on the charge generating layer to form a charge transporting layer having a thickness of about 15 $\mu m$.

The photosensitive member thus produce was charged by corona discharge at $-6.0$ kV for 0.2 second and examined with respect to electrophotographic characteristics in the same manner as in Example I-5. Good results were obtained, namely $V_s = -760$ V and $E_{\frac{1}{2}} = 4.6$ lux·sec.

EXAMPLE I-7

Photosensitive members were produced by forming respective photosensitive layers in substantially the same manner as in Example I-4 except that compound Nos. I-6 to I-32 were respectively used instead of compound No. I-3. Half decay exposure amounts were measured by using the electrostatic recording paper testing apparatus (Kawasaki Denki Model SP-428). The results are shown in Table 2, in which the half decay exposure amounts $E_{\frac{1}{2}}$ (lux·sec) are values obtained under the experimental conditions where the members were positively charged in the dark by corona discharge at $+6.0$ kV for 10 seconds and irradiated with white light at an illuminance of 2 luxes.

TABLE 2

| Compound No. | $E_{\frac{1}{2}}$ (lux · sec) |
|---|---|
| I-6 | 4.8 |
| I-7 | 5.1 |
| I-8 | 5.3 |
| I-9 | 5.5 |
| I-10 | 6.0 |
| I-11 | 6.0 |
| I-12 | 4.6 |
| I-13 | 5.9 |
| I-14 | 5.8 |
| I-15 | 5.5 |
| I-16 | 6.2 |
| I-17 | 6.0 |
| I-18 | 5.8 |
| I-19 | 6.6 |
| I-20 | 6.7 |
| I-21 | 7.2 |
| I-22 | 5.9 |
| I-23 | 6.6 |
| I-24 | 5.8 |
| I-25 | 5.9 |
| I-26 | 5.2 |
| I-27 | 4.9 |
| I-28 | 6.3 |
| I-29 | 6.5 |
| I-30 | 7.0 |
| I-31 | 5.8 |
| I-32 | 5.1 |

As can be seen in Table 2, the photosensitive members using the respective hydrazone compounds Nos. I-6 to I-32 were satisfactory with respect to the half decay exposure amount $E_{\frac{1}{2}}$, namely, sensitivity.

A description will now be made of a hydrazone compound prepared by a condensation reaction of a carbonyl compound of the formula: Ar—CHO, with a hydrazine compound of the formula:

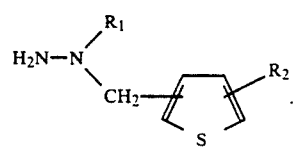

A carbonyl compound is condensed with a hydrazine compound in an alcohol such as ethanol in the presence of a small amount of a catalyst such as hydrochloric acid if necessary evolving water, according to the following reaction formula:

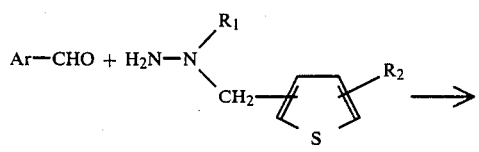

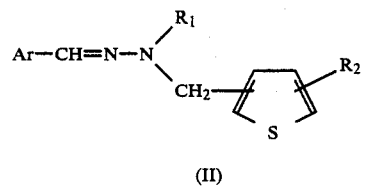

to synthesize a hydrazone compound of the above-mentioned general formula (II). In formula (II), $R_1$ stands for an aryl group which may have at least one substituent; $R_2$ stands for a hydrogen atom, a halogen atom, an alkyl group, an aryl group, or a nitro group; and Ar stands for a condensed-ring polycyclic aromatic hydrocarbon group which may have at least one substituent.

Specific examples of hydrazone compounds of general formula (II) prepared in the above-mentioned manner include:

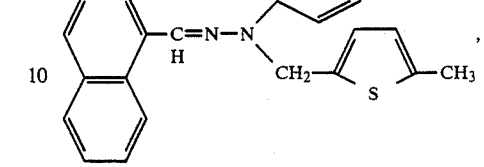

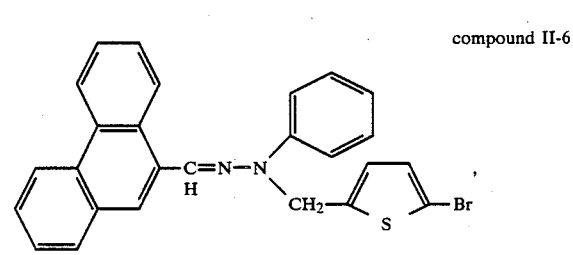

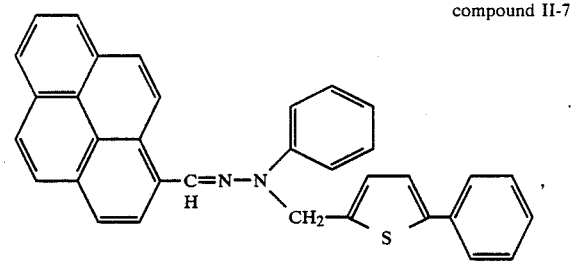

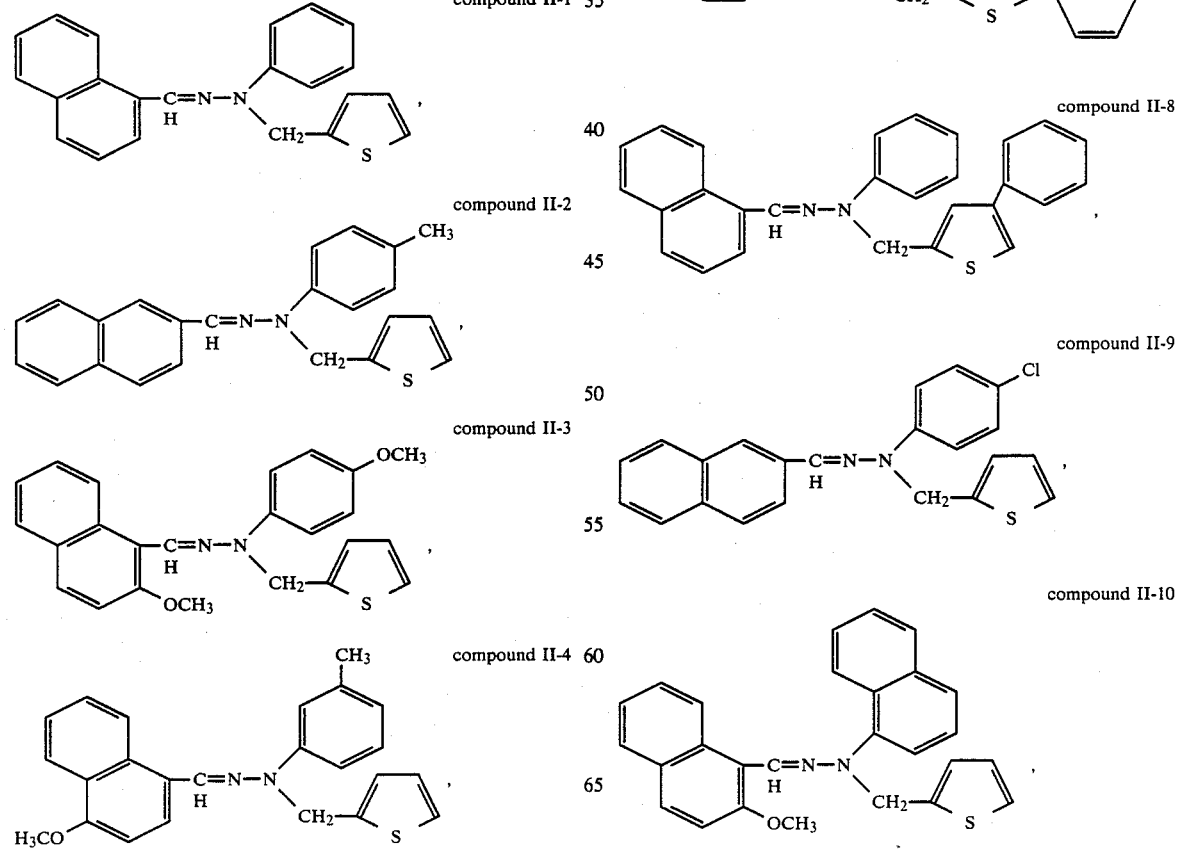

-continued compound II-11
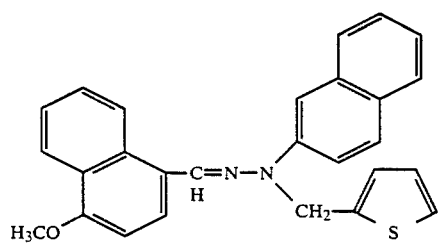

compound II-12
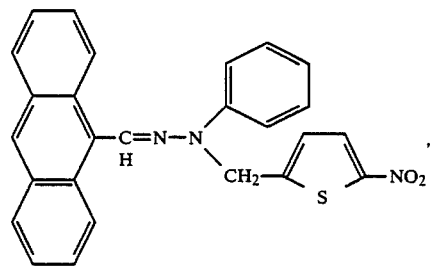

compound II-13
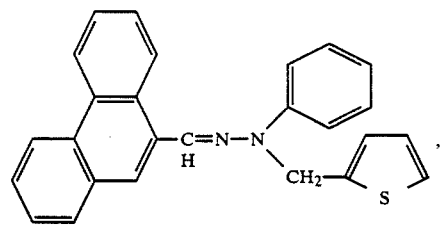

compound II-14
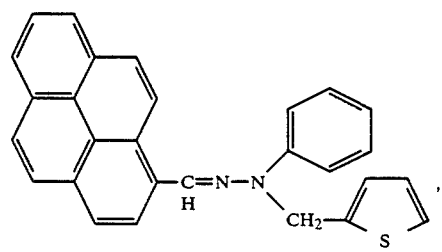

compound II-15
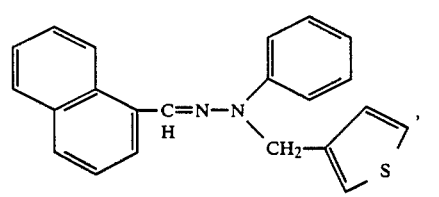

compound II-16
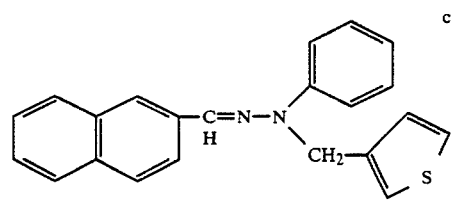

compound II-17
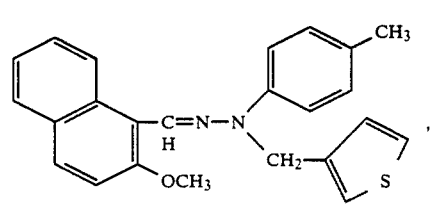

-continued compound II-18
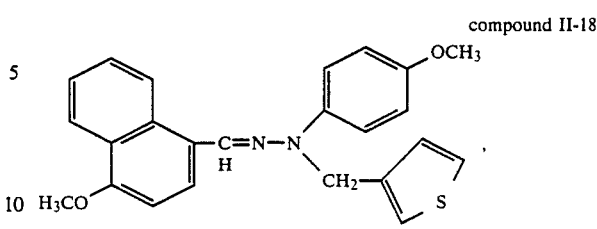

compound II-19
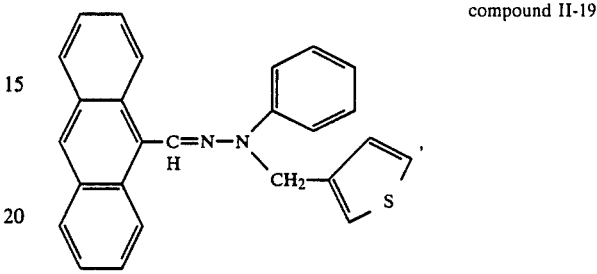

compound II-20
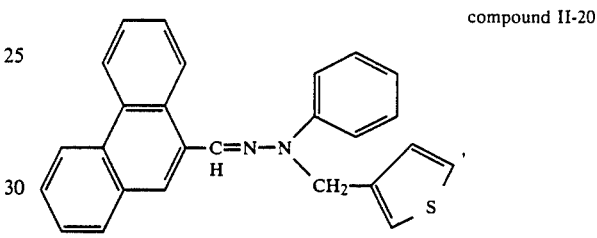

and compound II-21
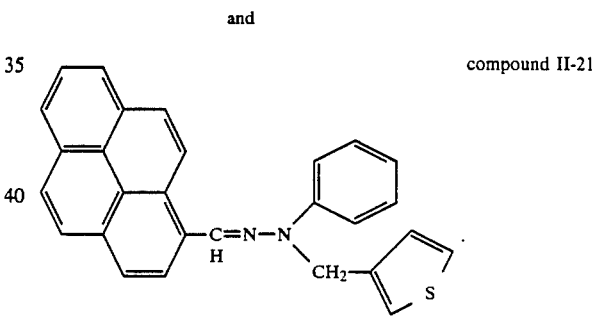

Examples will now be given, wherein various compounds represented by general formula (II) were respectively used to produce photosensitive members.

EXAMPLE II-1

A photosensitive member having the structure shown in FIG. 1 and comprising a photosensitive layer having a thickness of 15 μm was produced in substantially the same manner as in Example I-1 except that hydrazone compound No. II-1 mentioned above was used instead of the compound No. I-1.

EXAMPLE II-2

A photosensitive member having a structure corresponding to that of FIG. 3 but having no covering layer was produced in substantially the same manner as in Example I-2 except that hydrazone compound No. II-2 was used instead of compound No. I-2. The thickness of the charge transporting layer of the member was 15 μm, while the thickness of the charge generating layer was 1 μm.

EXAMPLE II-3

A photosensitive member was produced by forming a photosensitive layer in substantially the same manner as in Example II-1 except that 50 parts by weight of metal-free phthalocyanine, 100 parts by weight of the hydrazone compound No. II-3 mentioned above, 50 parts by weight of a polyester resin (Vylon 200), and 50 parts by weight of PMMA were used in place of the composition of the photosensitive layer of Example II-1.

EXAMPLE II-4

A photosensitive member was produced by forming a photosensitive layer in substantially the same manner as in Example II-3 except that Chlorodiane Blue was used instead of metal-free phthalocyanine.

The four photosensitive members thus produced were examined with respect to surface potential $V_s$, residual potential $V_r$, and half decay exposure amount $E_{\frac{1}{2}}$ by using white light as well as a monochromatic light (wavelength: 780 nm) in the same manner as in Examples I-1 to I-4. The results of the measurements are shown in Table 3.

TABLE 3

| Example No. | White Light | | | Light with Wavelength of 780 nm | | |
|---|---|---|---|---|---|---|
| | $V_s$ (volts) | $V_r$ (volts) | $E_{\frac{1}{2}}$ (lux·sec) | $V_s$ (volts) | $V_r$ (volts) | $E_{\frac{1}{2}}$ (μJ/cm$^2$) |
| II-1 | 730 | 80 | 5.1 | 720 | 70 | 4.8 |
| II-2 | 730 | 90 | 4.9 | 750 | 60 | 4.2 |
| II-3 | 700 | 70 | 5.4 | 700 | 50 | 4.5 |
| II-4 | 680 | 60 | 5.0 | — | — | — |

As can be seen in Table 3, the photosensitive members of Examples II-1, II-2, II-3 and II-4 were not substantially different therebetween in the half decay exposure amount and the residual potential, and showed good surface potential characteristics. The photosensitive members of Examples II-1, II-2 and II-3, using a phthalocyanine compound as a charge generating substance, showed also excellent electrophotographic characteristics for light with the long wavelength of 780 nm.

EXAMPLE II-5

A photosensitive member with the structure shown in FIG. 2 was produced by forming a charge generating layer and a charge transporting layer having a dry thickness of 20 μm in the same manner as in Example I-5 except that hydrazone compound No. II-4 was used instead of compound No. I-4. After this photosensitive member was charged by corona discharge at −6.0 kV for 0.2 second, the electrophotographic characteristics of the member were measured. Good results were obtained, namely $V_s = -650$ V, $V_r = -50$ V, and $E_{\frac{1}{2}} = 4.1$ lux·sec.

EXAMPLE II-6

A charge generating layer with a thickness of about 1 μm was formed on an aluminum support in the same manner as in Example I-6. A charge transporting layer with a thickness of about 15 μm was formed on the charge generating layer in substantially the same manner as in Example I-6 except that hydrazone compound No. II-5 was used instead of compound No. I-5.

The photosensitive member thus obtained was charged by corona discharge at −6.0 kV for 0.2 second and examined with respect to electrophotographic characteristics in the same manner as in Example II-5. Good results were obtained, namely $V_s = -700$ V and $E_{\frac{1}{2}} = 5.2$ lux·Sec.

EXAMPLE II-7

Photosensitive members were produced by forming respective photosensitive layers in substantially the same manner as in Example II-4 except that compounds Nos. II-6 to II-21 were respectively used instead of compound No. II-3. The half decay exposure amounts were measured by using the electrostatic recording paper testing apparatus Model SP-428. The results are shown in Table 4, in which the half decay exposure amounts $E_{\frac{1}{2}}$ (lux·sec) are values obtained under the experimental conditions where the members were positively charged in the dark by corona discharge at +6.0 kV for 10 seconds and irradiated with white light at an illuminance of 2 luxes.

TABLE 4

| Compound No. | $E_{\frac{1}{2}}$(lux · sec) |
|---|---|
| II-6 | 5.4 |
| II-7 | 5.1 |
| II-8 | 6.3 |
| II-9 | 6.3 |
| II-10 | 6.1 |
| II-11 | 5.4 |
| II-12 | 5.8 |
| II-13 | 6.0 |
| II-14 | 5.2 |
| II-15 | 4.9 |
| II-16 | 5.0 |
| II-17 | 6.1 |
| II-18 | 5.2 |
| II-19 | 6.1 |
| II-20 | 6.5 |
| II-21 | 6.8 |

As can be seen in Table 4, the photosensitive members using the respective hydrazone compounds Nos. II-6 to II-21 were satisfactory with respect to the half decay exposure amount $E_{\frac{1}{2}}$, namely, sensitivity.

A description will now be made of a hydrazone compound prepared using a carbonyl compound of the formula:

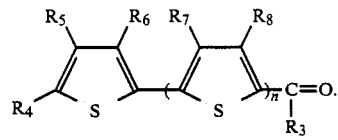

A carbonyl compound is condensed with a hydrazine compound in an alcohol such as ethanol in the presence of a small amount of a catalyst such as hydrochloric acid if necessary, evolving water, according to the following reaction formula:

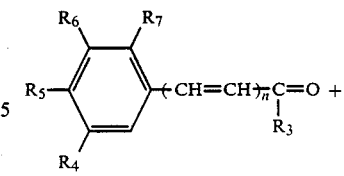

-continued

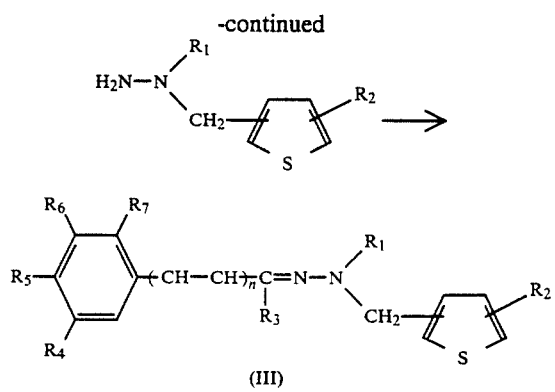

to synthesize a hydrazone compound of the above-mentioned general formula (III). In the general formula (III), $R_1$ stands for an aryl group which may have at least one substituent; each of $R_2$, $R_3$, $R_4$, $R_5$, $R_6$ and $R_7$ stands for a hydrogen atom, a halogen atom, an alkyl group, an alkoxy group, a phenoxy group, a nitro group, a hydroxy group, an aryl group, or a styryl group; and n stands for an integer of 0 or 1.

Specific examples of hydrazone compounds of general formula (III) prepared in the above-mentioned manner include:

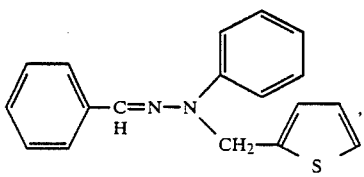

compound III-1

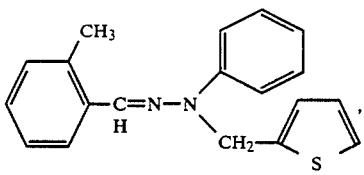

compound III-2

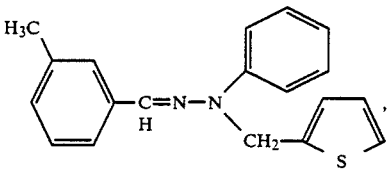

compound III-3

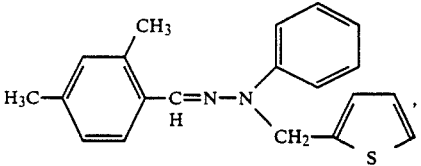

compound III-4

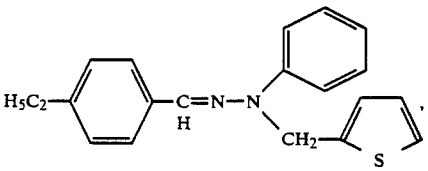

compound III-5

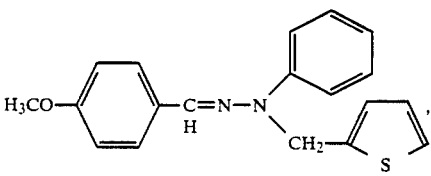

compound III-6

-continued
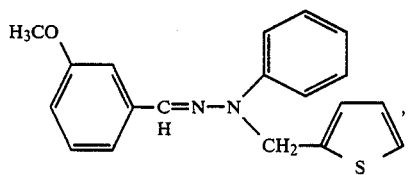 compound III-7
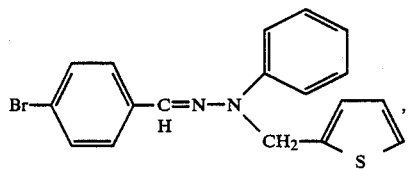 compound III-8
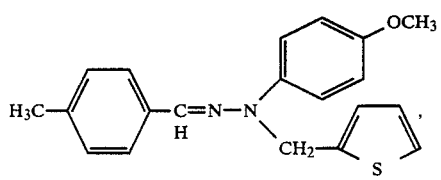 compound III-9
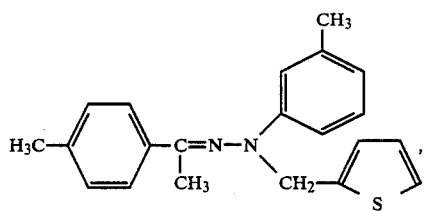 compound III-10
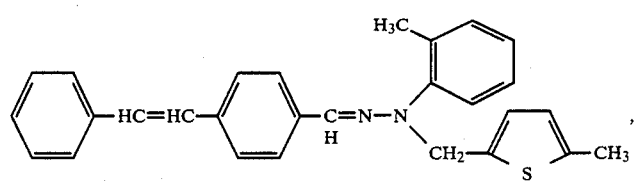 compound III-11
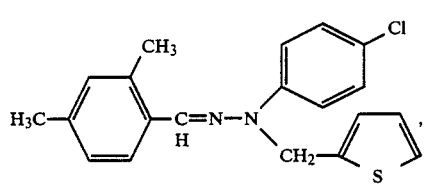 compound III-12
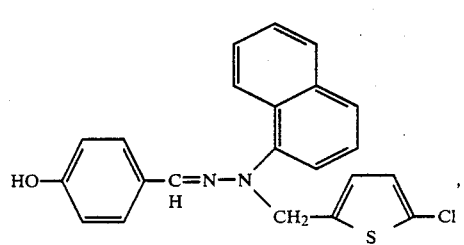 compound III-13

-continued
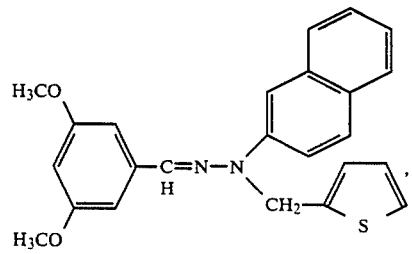
compound III-14
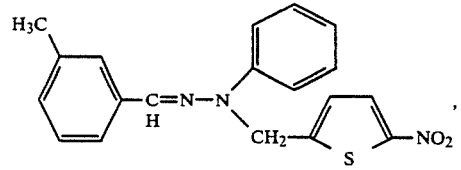
compound III-15
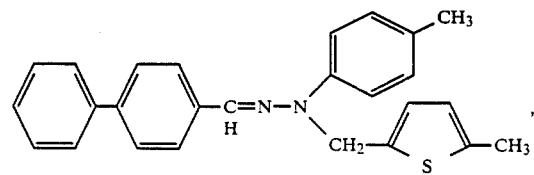
compound III-16
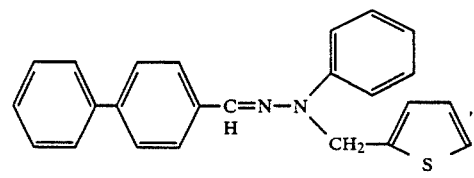
compound III-17
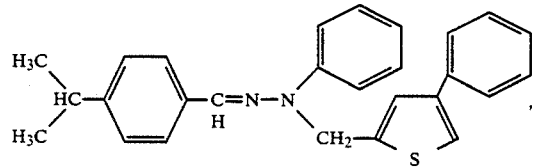
compound III-18
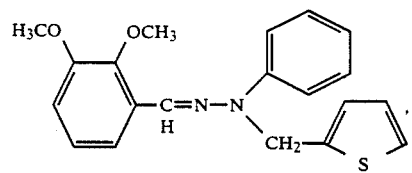
compound III-19
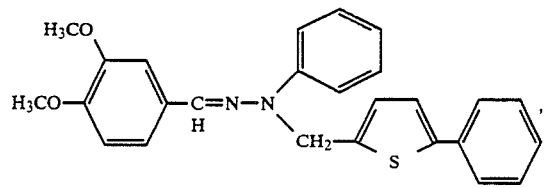
compound III-20
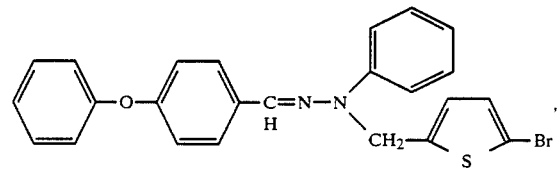
compound III-21

-continued
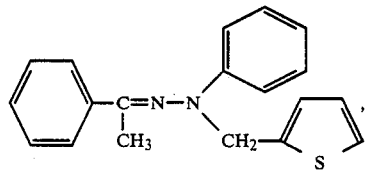
compound III-22
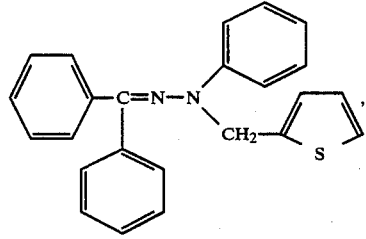
compound III-23
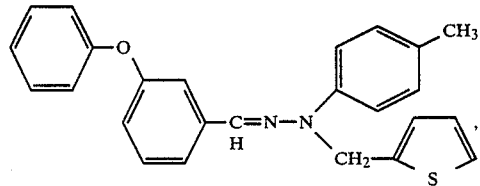
compound III-24
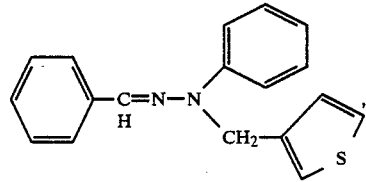
compound III-25
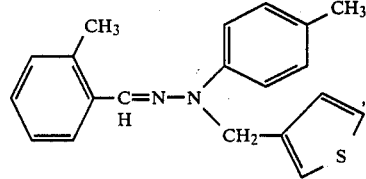
compound III-26
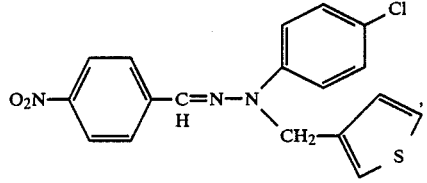
compound III-27
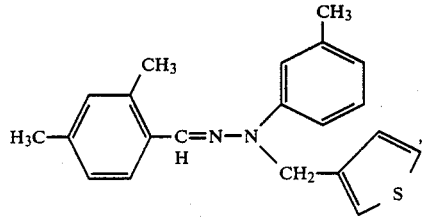
compound III-28

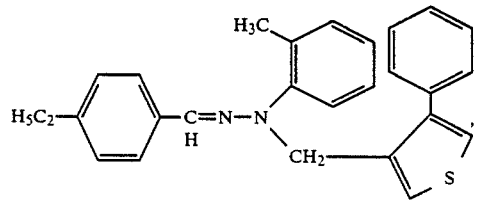
compound III-29
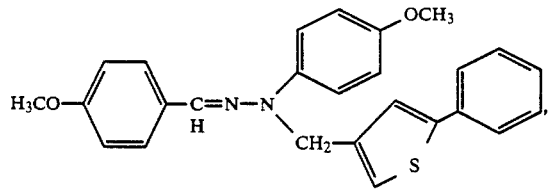
compound III-30
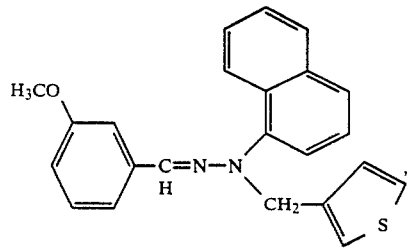
compound III-31
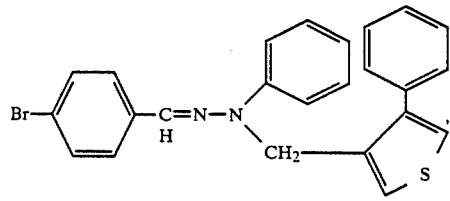
compound III-32
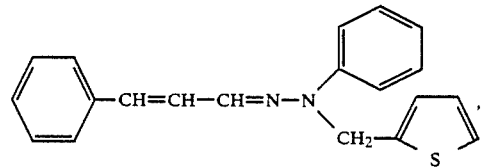
compound III-33
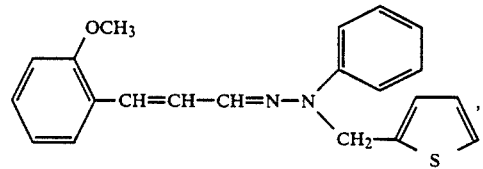
compound III-34
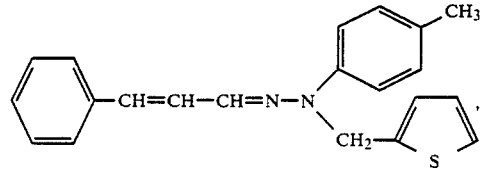
compound III-35

-continued

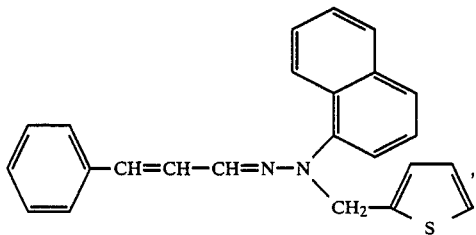
compound III-36

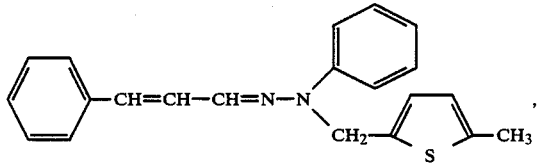
compound III-37

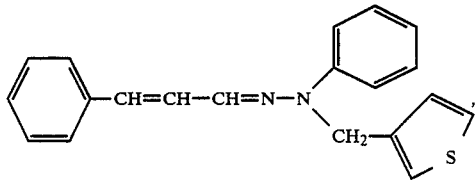
compound III-38

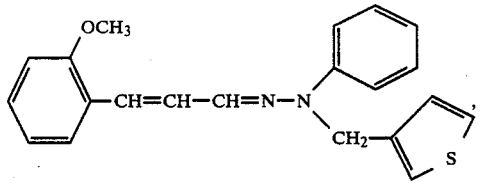
compound III-39 and

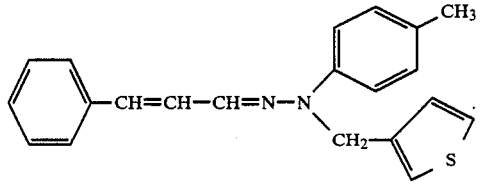
compound III-40

Examples of a photosensitive member, in which a chemical compound represented by general formula (III) is used as a charge transporting substance, will be explained.

EXAMPLE III-1

A photosensitive member having the structure shown in FIG. 1 and comprising a photosensitive layer having a thickness of 15 μm was produced in substantially the same manner as in Example I-1 except that hydrazone compound No. III-1 mentioned above was used instead of compound No. I-1.

EXAMPLE III-2

A photosensitive member having a structure corresponding to that of FIG. 3 but having no covering layer was produced in substantially the same manner as in Example I-2 except that hydrazone compound No. III-2 was used instead of compound No. I-2. The thickness of the charge transporting layer of the member was 15 μm while the thickness of the charge generating layer was 1 μm.

EXAMPLE III-3

A photosensitive member was produced by forming a photosensitive layer in substantially the same manner as in Example III-1 except that 50 parts by weight of metal-free phthalocyanine, 100 parts by weight of the hydrazone compound No. III-3 mentioned above, 50 parts by weight of a polyester resin (Vylon 200), and 50 parts by weight of PMMA were used to replace therewith the composition of the photosensitive layer of Example III-1.

EXAMPLE III-4

A photosensitive member was produced by forming a photosensitive layer in substantially the same manner as in Example III-3 except that Chlorodiane Blue was used instead of metal-free phthalocyanine.

The four photosensitive members thus produced were examined with respect to surface potential $V_s$, residual potential $V_r$, and half decay exposure amount $E_{\frac{1}{2}}$ by using white light as well as a monochromatic light (wavelength: 780 nm) in the same manner as in Examples I-1 to I-4. The results of the measurements are shown in Table 5.

TABLE 5

| Exam- ple No. | White Light | | | Light with Wavelength of 780 nm | | |
|---|---|---|---|---|---|---|
| | $V_s$ (volts) | $V_r$ (volts) | $E_{\frac{1}{2}}$ (lux · sec) | $V_s$ (volts) | $V_r$ (volts) | $E_{\frac{1}{2}}$ (μJ/cm²) |
| III-1 | 710 | 60 | 5.2 | 700 | 50 | 5.0 |
| III-2 | 730 | 80 | 5.4 | 690 | 100 | 5.8 |
| III-3 | 700 | 60 | 5.9 | 690 | 50 | 5.7 |
| III-4 | 690 | 60 | 5.0 | — | — | — |

As can be seen in Table 5, the photosensitive members of Examples III-1, III-2, III-3 and III-4 were not substantially different therebetween in the half decay exposure amount and the residual potential, and showed good surface potential characteristics. The photosensitive members of Examples III-1, III-2 and III-3, using a phthalocyanine compound as the charge generating substance, showed also excellent electrophotographic characteristics for light with the long wavelength of 780 nm.

EXAMPLE III-5

A photosensitive member with the structure shown in FIG. 2 was produced by forming a charge generating layer and a charge transporting layer having a dry thickness of 20 μm in substantially the same manner as in Example I-5 except that hydrazone compound No. III-4 was used instead of compound No. I-4: After this photosensitive member was charged by corona discharge at −6.0 kV and for 0.2 second, the electrophotographic characteristics of the member were measured. Good results were obtained, namely $V_s = -650$ V, $V_r = -80$ V, and $E_{\frac{1}{2}} = 4.8$ lux·sec.

EXAMPLE III-6

A charge generating layer having a thickness of about 1 μm was formed on an aluminum support in the same manner as in Example I-6. A charge transporting layer having a thickness of about 15 μm was formed on the charge generating layer in substantially the same manner as in Example I-6 except that hydrazone compound No. III-5 was used instead of compound No. I-5.

The photosensitive member thus obtained was charged by corona discharge at −6.0 kV for 0.2 second and examined with respect to electrophotographic characteristics in the same manner as in Example III-5. Good results were obtained, namely $V_s = -680$ V and $E_{\frac{1}{2}} = 5.9$ lux·sec.

EXAMPLE III-7

Photosensitive members were produced by forming respective photosensitive layers in substantially the same manner as in Example III-4 except that compounds Nos. III-6 to III-40 were respectively used instead of compound No III-3, and were examined with respect to half decay exposure amount by using the electrostatic recording paper testing apparatus Model SP-428. The results are shown in Table 6, in which the half decay exposure amounts $E_{\frac{1}{2}}$ (lux·sec) are values obtained under the experimental conditions where the members were positively charged in the dark by corona discharge at +6.0 kV for 10 seconds and irradiated with white light at an illuminance of 2 luxes.

TABLE 6

| Compound No. | $E_{\frac{1}{2}}$(lux · sec) |
|---|---|
| III-6 | 4.8 |
| III-7 | 6.3 |
| III-8 | 6.1 |
| III-9 | 5.3 |
| III-10 | 5.6 |
| III-11 | 6.2 |
| III-12 | 5.8 |
| III-13 | 4.6 |
| III-14 | 5.8 |
| III-15 | 5.0 |
| III-16 | 5.9 |
| III-17 | 4.7 |
| III-18 | 6.1 |
| III-19 | 5.7 |
| III-20 | 6.3 |
| III-21 | 4.7 |
| III-22 | 5.8 |
| III-23 | 6.2 |
| III-24 | 5.1 |
| III-25 | 6.0 |
| III-26 | 6.3 |
| III-27 | 5.4 |
| III-28 | 5.6 |
| III-29 | 4.3 |
| III-30 | 5.2 |
| III-31 | 4.9 |
| III-32 | 6.7 |
| III-33 | 7.0 |
| III-34 | 6.5 |
| III-35 | 7.2 |
| III-36 | 5.8 |
| III-37 | 5.0 |
| III-38 | 5.5 |
| III-39 | 5.2 |
| III-40 | 6.9 |

As can be seen in Table 6, the photosensitive members using the respective hydrazone compounds Nos. III-6 to III-40 were satisfactory with respect to the half decay exposure amount $E_{\frac{1}{2}}$, namely sensitivity.

Description will now be made of a hydrazone compound prepared by using a carbonyl compound of the formula:

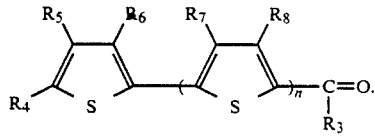

The carbonyl compound is condensed with a hydrazine compound in an alcohol such as ethanol in the presence of a small amount of a catalyst such as hydrochloric acid if necessary, evolving water according to the following reaction formula:

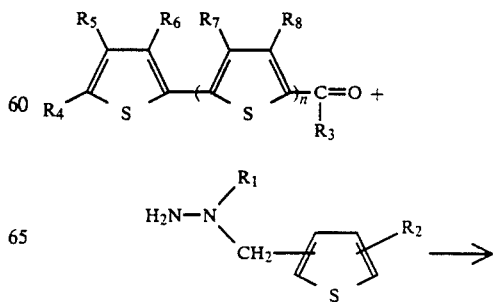

-continued

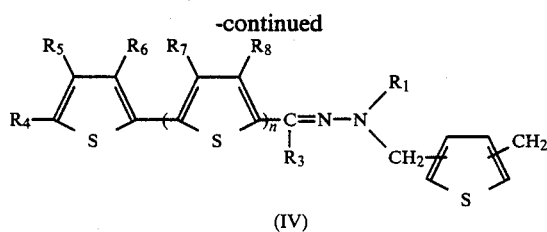

(IV)

to synthesize the hydrazone compound of the above-mentioned general formula (IV), $R_1$ stands for an aryl group which may have at least one substituent; each of $R_2$, $R_3$, $R_4$, $R_5$, $R_6$, $R_7$ and $R_8$ stands for a hydrogen atom, a halogen atom, an alkoxy group, an alkyl group, a nitro group, a hydroxy group, an aryl group, or an amino group which may have at least one substituent; and n stands for an integer of 1, 2, 3 or 4.

Specific examples of hydrazone compounds of general formula (IV) prepared in the above-mentioned manner include:

compound IV-1

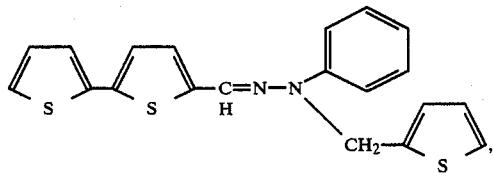

compound IV-2

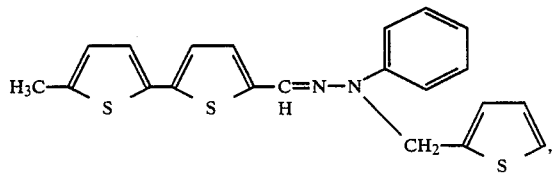

compound IV-3

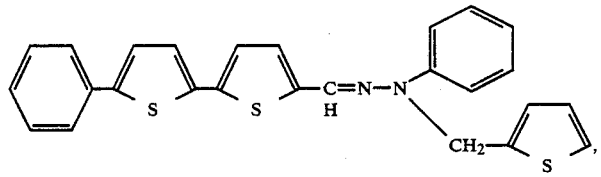

compound IV-4

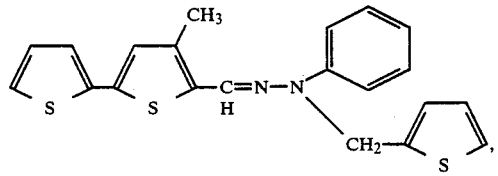

compound IV-5

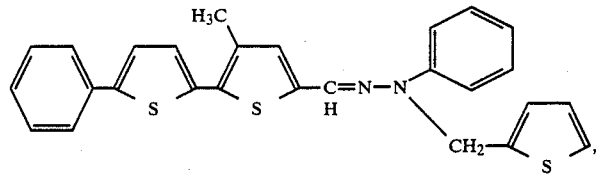

compound IV-6

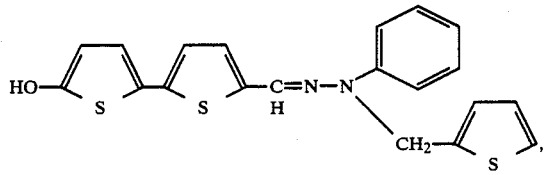

compound IV-7

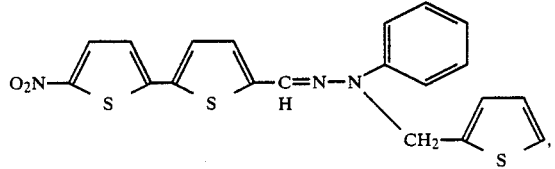

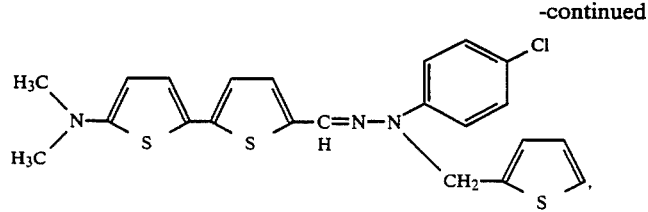
compound IV-8
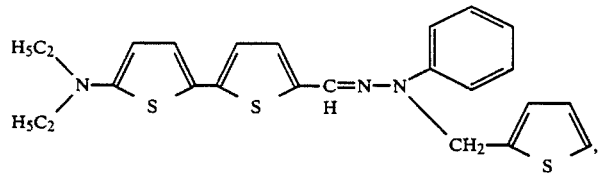
compound IV-9
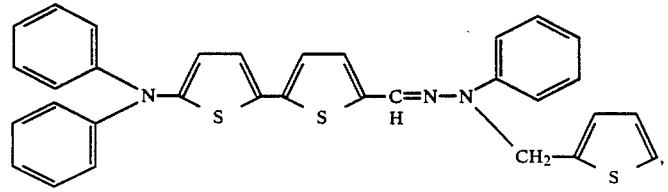
compound IV-10
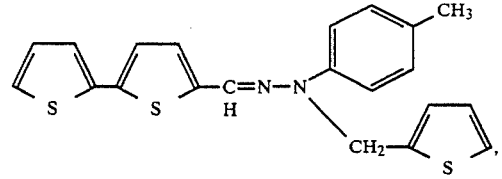
compound IV-11
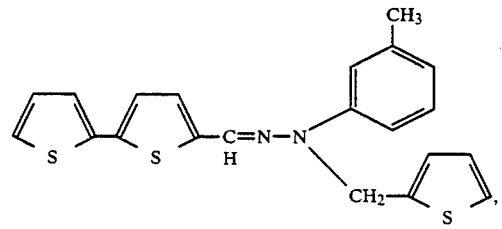
compound IV-12
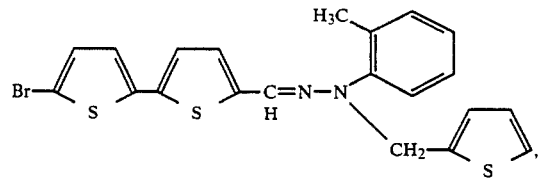
compound IV-13
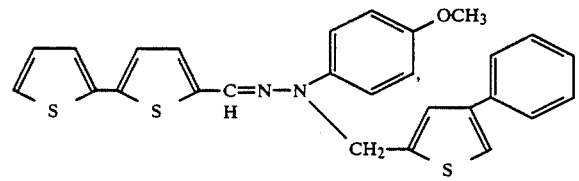
compound IV-14
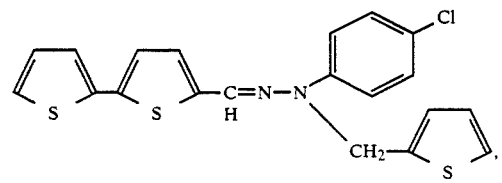
compound IV-15

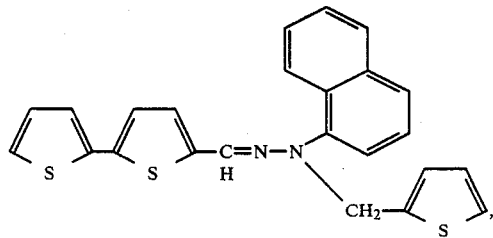
compound IV-16
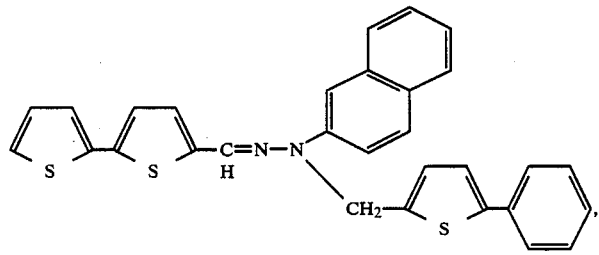
compound IV-17
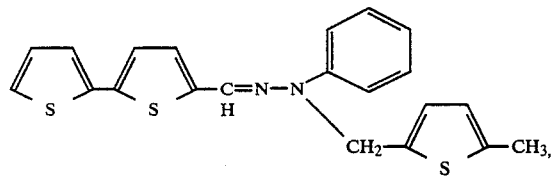
compound IV-18
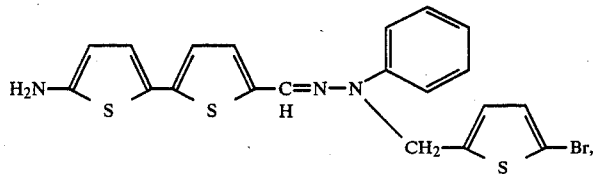
compound IV-19
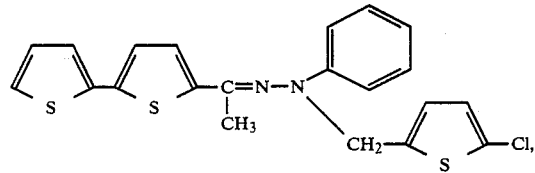
compound IV-20
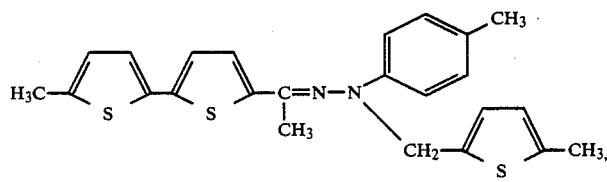
compound IV-21
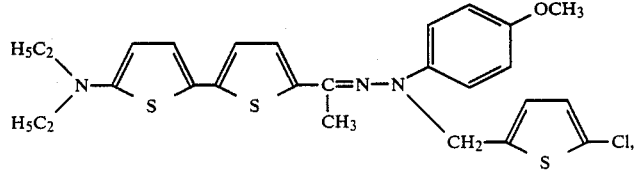
compound IV-22

-continued
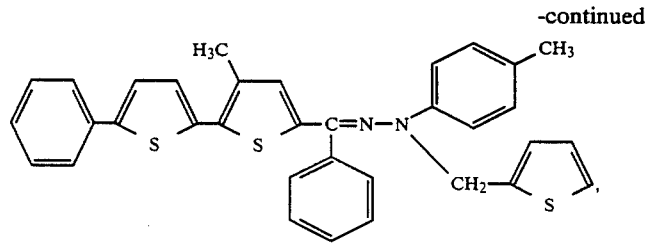
compound IV-23
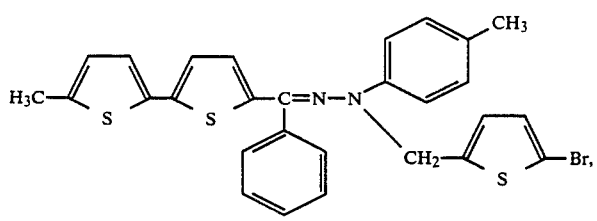
compound IV-24
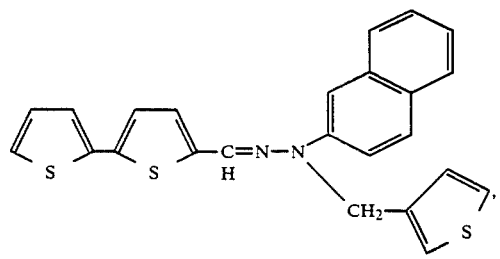
compound IV-25
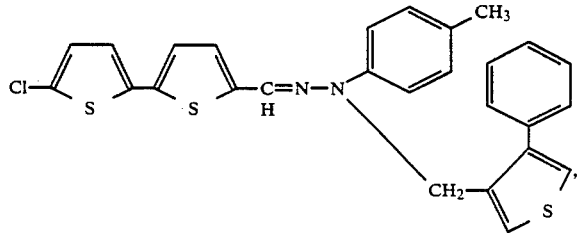
compound IV-26
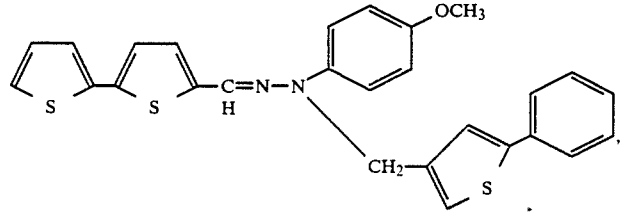
compound IV-27
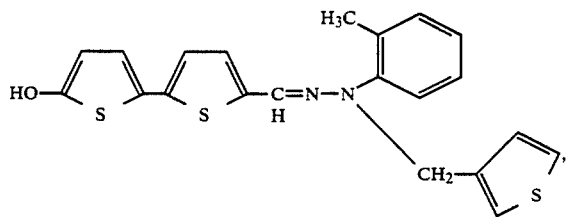
compound IV-28
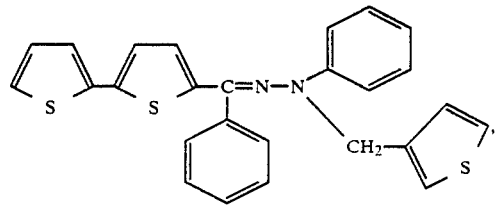
compound IV-29

-continued
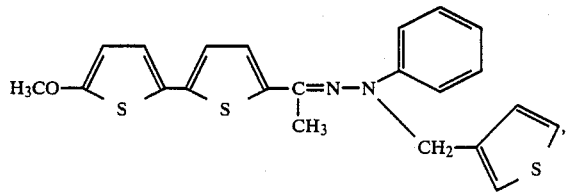
compound IV-30
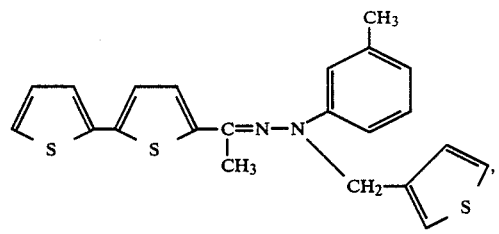
compound IV-31
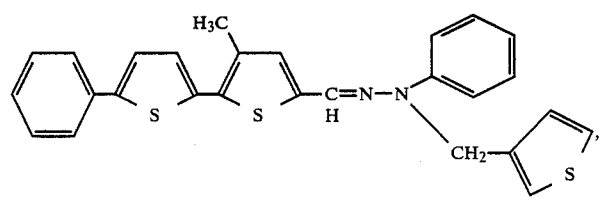
compound IV-32
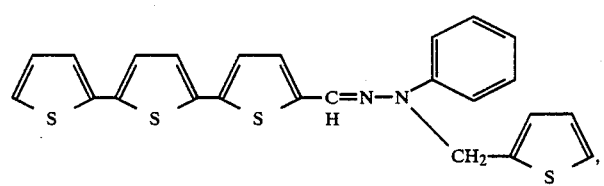
compound IV-33
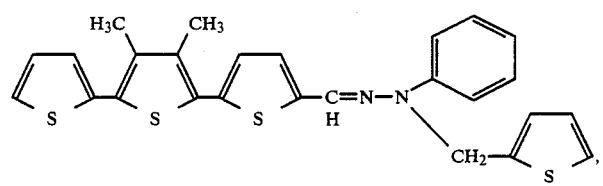
compound IV-34
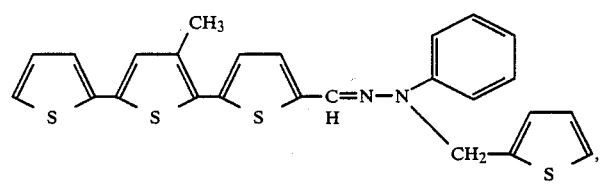
compound IV-35
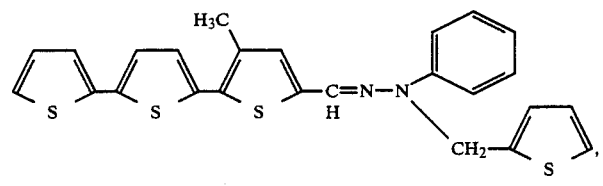
compound IV-36
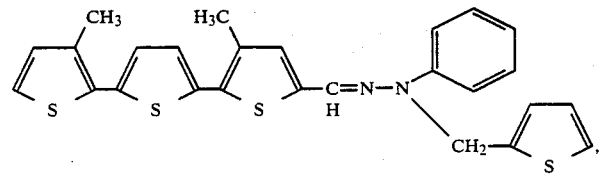
compound IV-37

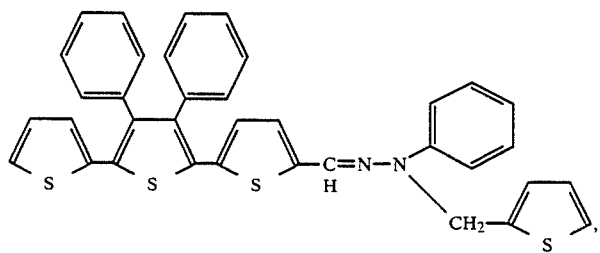
compound IV-38
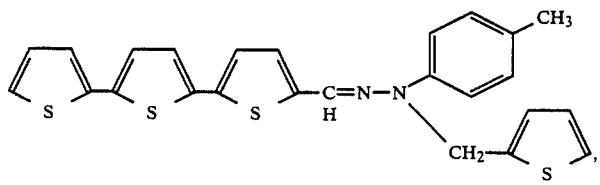
compound IV-39
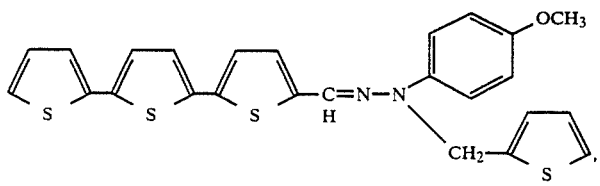
compound IV-40
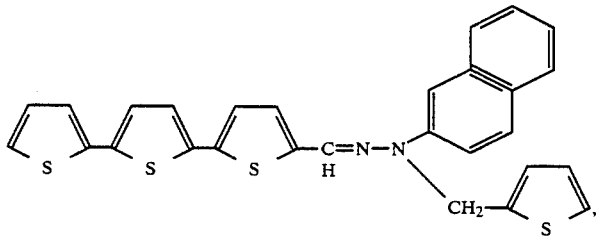
compound IV-41
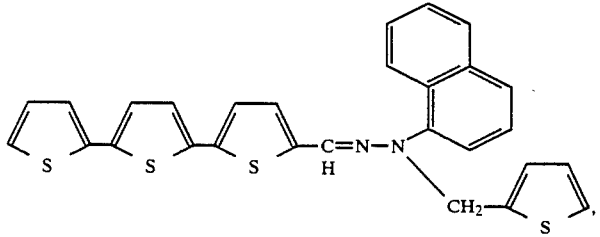
compound IV-42
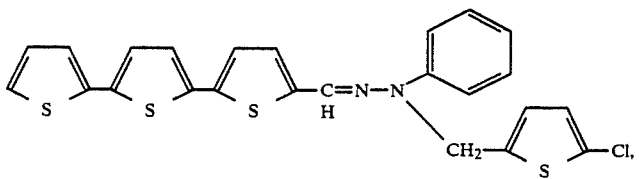
compound IV-43
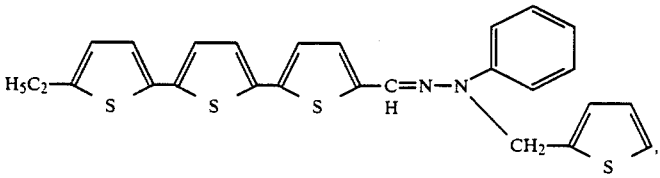
compound IV-44

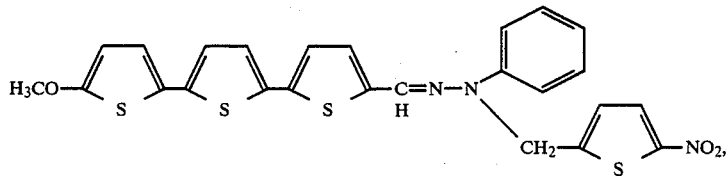
compound IV-45
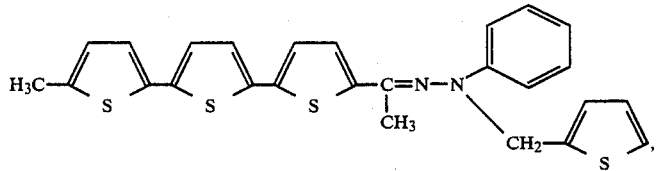
compound IV-46
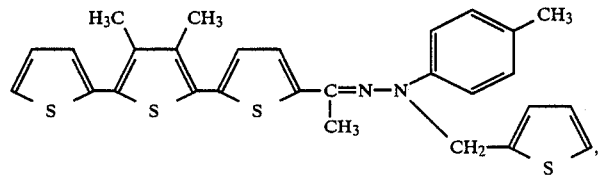
compound IV-47
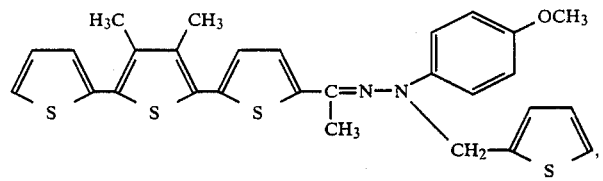
compound IV-48
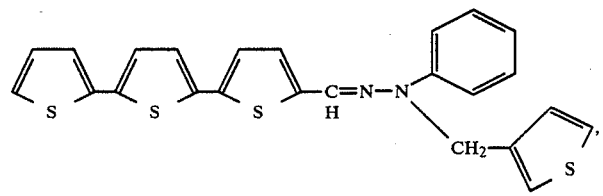
compound IV-49
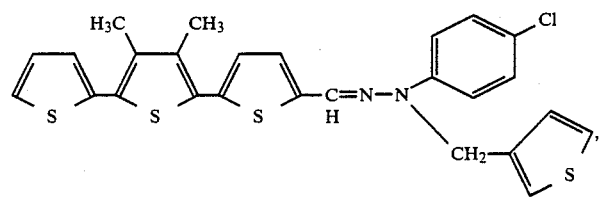
compound IV-50
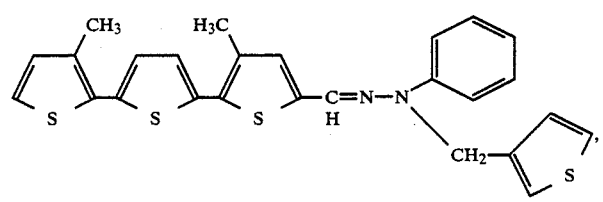
compound IV-51
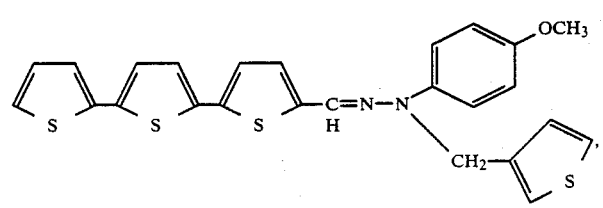
compound IV-52

-continued
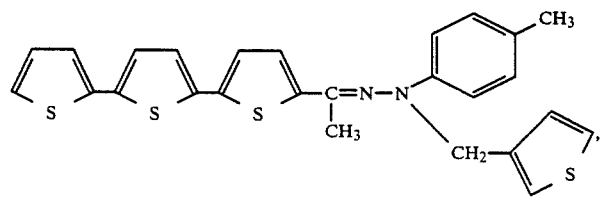 compound IV-53
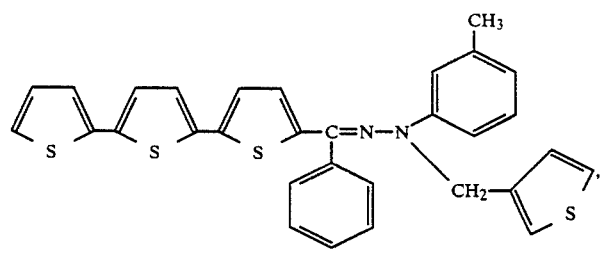 compound IV-54
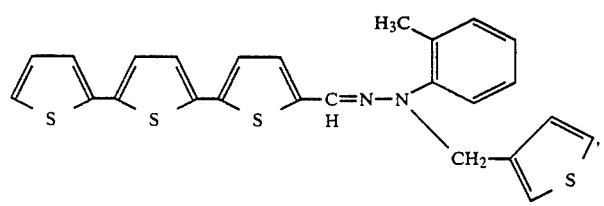 compound IV-55
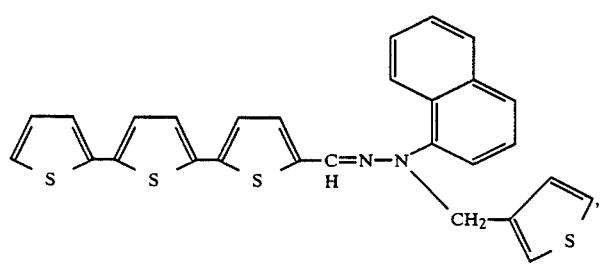 compound IV-56
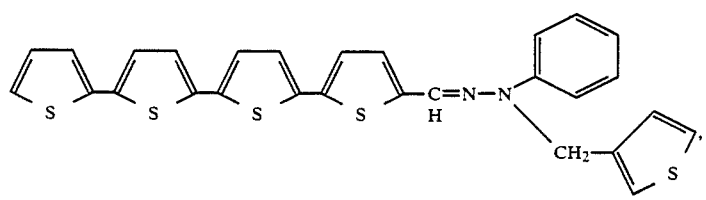 compound IV-57
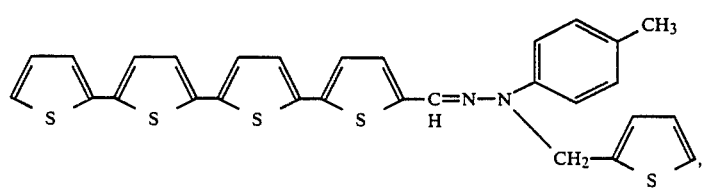 compound IV-58
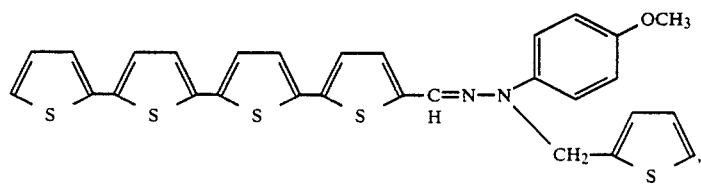 compound IV-59

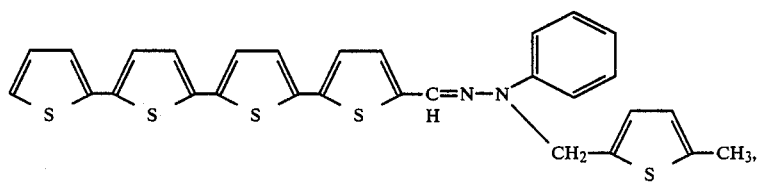
compound IV-60
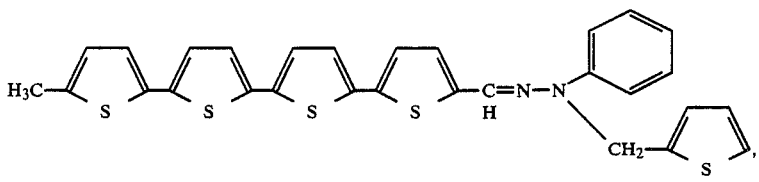
compound IV-61
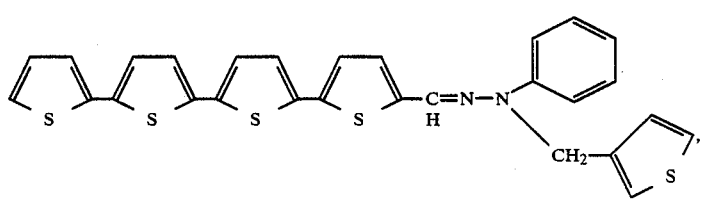
compound IV-62
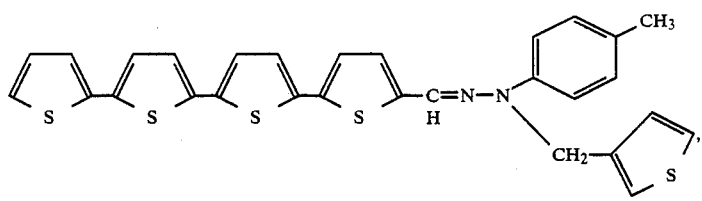
compound IV-63
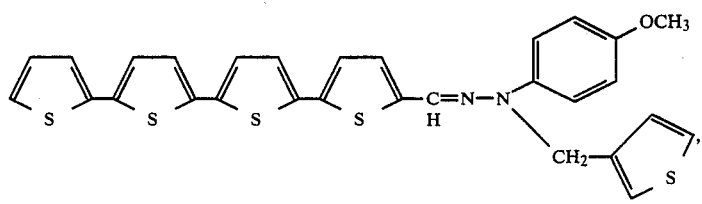
compound IV-64
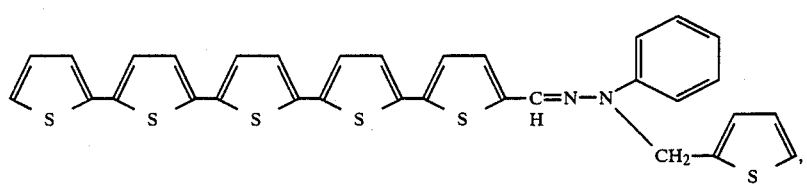
compound IV-65
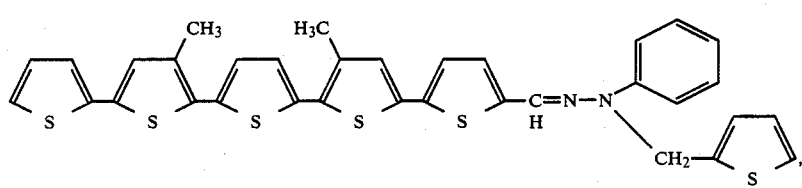
compound IV-66
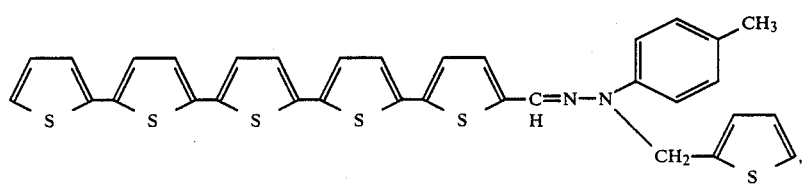
compound IV-67

-continued

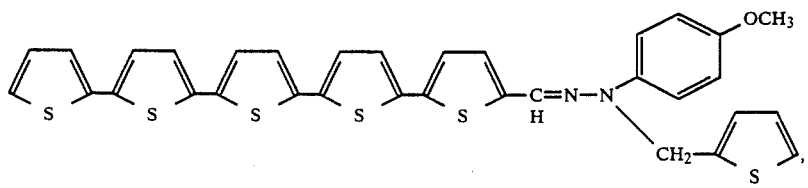

compound IV-68

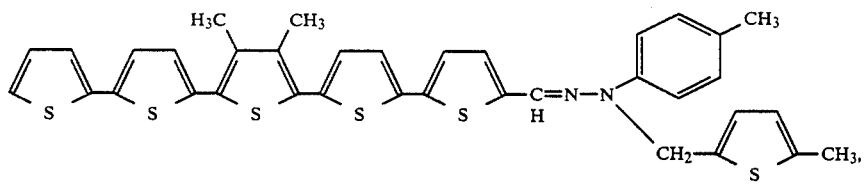

compound IV-69

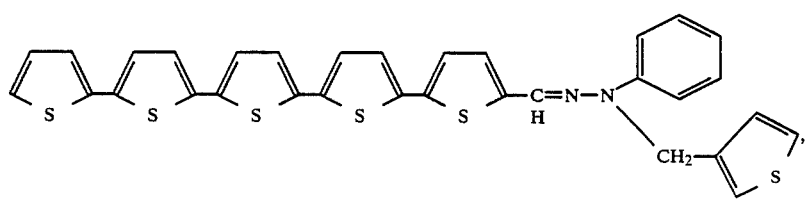

compound IV-70

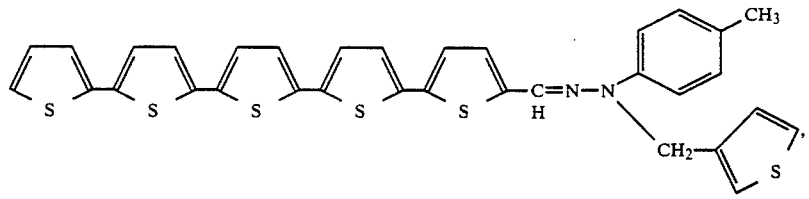

compound IV-71 and

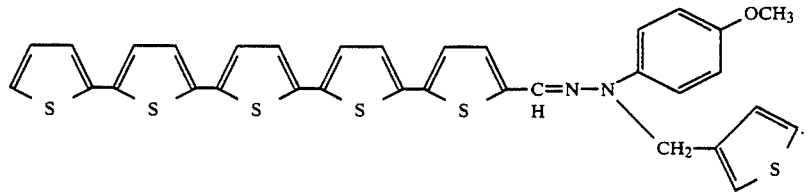

compound IV-72

Examples of a photosensitive member, in which a chemical compound represented by general formula (IV) is used as a charge transporting substance, will be explained.

EXAMPLE IV-1

A photosensitive member having the structure shown in FIG. 1 and comprising a photosensitive layer having a thickness of 15 μm was produced in substantially the same manner as in Example I-1 except that hydrazone compound No. IV-1 mentioned above was used instead of compound No. I-1.

EXAMPLE IV-2

A photosensitive member having a structure corresponding to that shown in FIG. 3 but having no covering layer was produced in substantially the same manner as in Example I-2 except that hydrazone compound No. IV-2 was used instead of compound No. I-2. The thickness of the charge transporting layer of the member was 15 μm, while the thickness of the charge generating layer was 1 μm.

EXAMPLE IV-3

A photosensitive member was produced by forming a photosensitive layer in substantially the same manner as in Example IV-1 except that 50 parts by weight of metal-free phthalocyanine, 100 parts by weight of hydrazone compound No. IV-3 mentioned above, 50 parts by weight of a polyester resin (Vylon 200) and 50 parts by weight of PMMA were used to replace therewith the composition of the photosensitive layer of Example IV-1.

EXAMPLE IV-4

A photosensitive member was produced by forming a photosensitive layer in substantially the same manner as in Example IV-3 except that Chlorodiane Blue was used instead of metal-free phthalocyanine.

The four photosensitive members thus produced were examined with respect to surface potential $V_s$, residual potential $V_r$, and half decay exposure amount $E_{\frac{1}{2}}$ by using white light as well as a monochromatic light (wavelength: 780 nm) in the same manner as in Examples I-1 to I-4. The results of the measurements are shown in Table 7.

TABLE 7

| Example No. | White Light | | | Light with Wavelength of 780 nm | | |
|---|---|---|---|---|---|---|
| | $V_s$ (volts) | $V_r$ (volts) | $E_{\frac{1}{2}}$ (lux·sec) | $V_s$ (volts) | $V_r$ (volts) | $E_{\frac{1}{2}}$ (μJ/cm²) |
| IV-1 | 730 | 80 | 4.8 | 700 | 70 | 4.5 |
| IV-2 | 720 | 90 | 4.9 | 680 | 70 | 4.3 |
| IV-3 | 780 | 80 | 5.4 | 720 | 60 | 4.8 |
| IV-4 | 700 | 60 | 4.7 | — | — | — |

As can be seen in Table 7, the photosensitive members of Examples IV-1, IV-2, IV-3 and IV-4 were not substantially different therebetween in the half decay exposure amount and the residual potential, and showed good surface potential characteristics. The photosensitive members of Examples IV-1, IV-2 and IV-3, using a phthalocyanine compound as the charge generating substance, showed also excellent electrophotographic characteristics for light with the long wavelength of 780 nm.

EXAMPLE IV-5

A photosensitive member with the structure shown in FIG. 2 was produced by forming a charge generating layer and a charge transporting layer having a dry thickness of 20 μm in substantially the same manner as in Example I-5 except that hydrazone compound No. IV-4 was used instead of compound No. I-4. This photosensitive member was charged by corona discharge at −6.0 kV for 0.2 second and examined with respect to electrophotographic characteristics. Good results were obtained, namely $V_s = -700$ V, $V_r = -100$ V and $E_{\frac{1}{2}} = 4.0$ lux·sec.

EXAMPLE IV-6

A charge generating layer having at thickness of about 1 μm was formed on an aluminum support in the same manner as in Example I-6. A charge transporting layer having a thickness of about 15 μm was formed on the charge generating layer in substantially the same manner as in Example I-6 except that hydrazone compound No. IV-5 was used instead of compound No. I-5.

After the photosensitive member thus obtained was charged by corona discharge at −6.0 kV for 0.2 second, the electrophotographic characteristics of the member were measured in the same manner as in Example IV-5. Good results were obtained, namely $V_s = -750$ V and $E_{\frac{1}{2}} = 5.2$ lux·sec.

EXAMPLE IV-7

Photosensitive members were produced by forming respective photosensitive layers in substantially the same manner as in Example IV-4 except that the compounds Nos. IV-6 to IV-72 were respectively used instead of the compound No. IV-3, and were examined with respect to half decay exposure amount by using the electrostatic recording paper testing apparatus Model SP-428. The results are shown in Table 8, in which the half decay exposure amounts $E_{\frac{1}{2}}$ (lux·sec) are values obtained under the experimental conditions where the members were positively charged in the dark by corona discharge at +6.0 kV for 10 seconds and irradiated with white light at an illuminance of 2 luxes.

TABLE 8

| Compound No. | $E_{\frac{1}{2}}$ (lux·sec) |
|---|---|
| IV-6 | 5.5 |
| IV-7 | 4.9 |
| IV-8 | 5.8 |
| IV-9 | 5.2 |
| IV-10 | 6.0 |
| IV-11 | 6.1 |
| IV-12 | 5.7 |
| IV-13 | 4.8 |
| IV-14 | 6.0 |
| IV-15 | 5.9 |
| IV-16 | 5.9 |
| IV-17 | 5.2 |
| IV-18 | 5.4 |
| IV-19 | 4.9 |
| IV-20 | 5.0 |
| IV-21 | 6.2 |
| IV-22 | 6.0 |
| IV-23 | 5.7 |
| IV-24 | 6.3 |
| IV-25 | 6.1 |
| IV-26 | 5.4 |
| IV-27 | 5.5 |
| IV-28 | 5.8 |
| IV-29 | 4.8 |
| IV-30 | 5.7 |
| IV-31 | 5.7 |
| IV-32 | 5.7 |
| IV-33 | 4.8 |
| IV-34 | 5.5 |
| IV-35 | 4.9 |
| IV-36 | 5.0 |
| IV-37 | 5.3 |
| IV-38 | 5.2 |
| IV-39 | 4.9 |
| IV-40 | 4.6 |
| IV-41 | 4.2 |
| IV-42 | 5.0 |
| IV-43 | 5.7 |
| IV-44 | 5.6 |
| IV-45 | 5.5 |
| IV-46 | 4.6 |
| IV-47 | 6.0 |
| IV-48 | 5.8 |
| IV-49 | 5.4 |
| IV-50 | 6.0 |
| IV-51 | 5.1 |
| IV-52 | 5.3 |
| IV-53 | 5.8 |
| IV-54 | 5.6 |
| IV-55 | 5.6 |
| IV-56 | 4.9 |
| IV-57 | 4.6 |
| IV-58 | 6.7 |
| IV-59 | 6.1 |
| IV-60 | 5.9 |
| IV-61 | 6.0 |
| IV-62 | 5.2 |
| IV-63 | 5.8 |
| IV-64 | 5.3 |
| IV-65 | 6.0 |
| IV-66 | 4.9 |
| IV-67 | 6.1 |
| IV-68 | 5.8 |
| IV-69 | 5.7 |
| IV-70 | 5.2 |
| IV-71 | 5.3 |
| IV-72 | 5.3 |

As can be seen in Table 8, the photosensitive members using the respective hydrazone compounds Nos. IV-6 to IV-72 were satisfactory with respect to half decay exposure amount $E_{\frac{1}{2}}$, namely sensitivity.

A description will now be made of a hydrazone compound prepared by using a carbonyl compound of the formula:

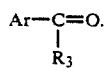

A carbonyl compound is condensed with a hydrazine compound in an alcohol such as ethanol in the presence of a small amount of a catalyst such as hydrochloric acid if necessary evolving water, according to the following reaction formula:

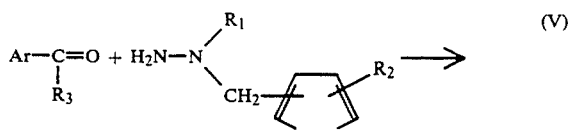

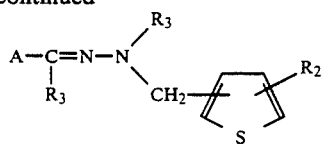

to synthesize a hydrazone compound of the above-mentioned general formula (V). In general formula (V), $R_1$ stands for an aryl group which may have at least one substituent; each of $R_2$ and $R_3$ stands for a hydrogen atom, a halogen atom, an alkyl group, an alkoxy group, an aryl group, or a nitro group; and Ar stands for a heterocyclic group which may have at least one substituent.

Specific examples of hydrazone compounds of general formula (V) prepared in the above-mentioned manner include:

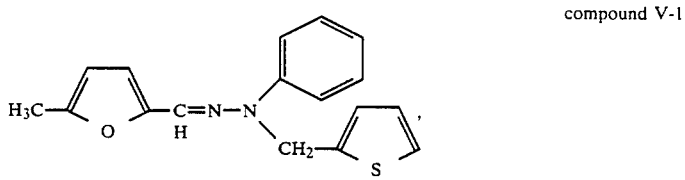
compound V-1

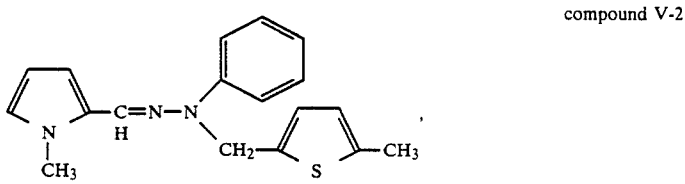
compound V-2

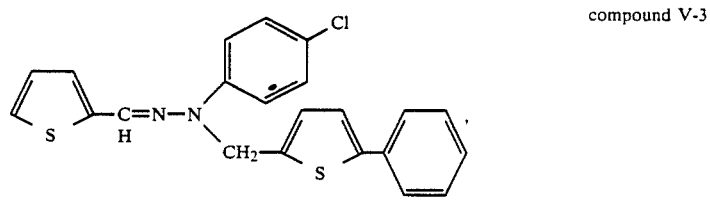
compound V-3

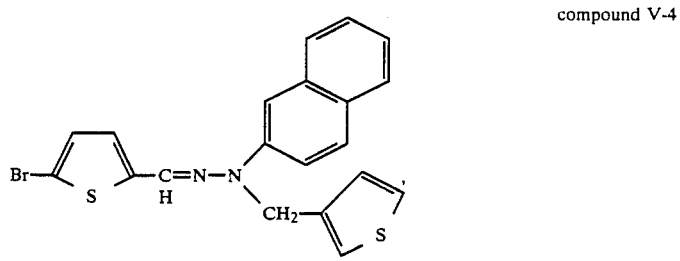
compound V-4

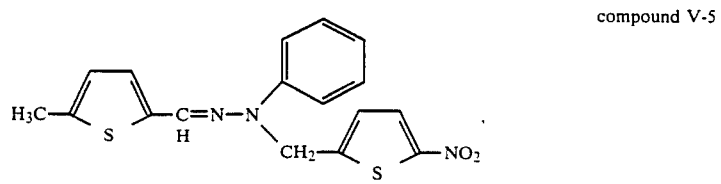
compound V-5

-continued
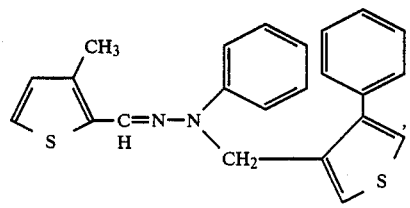
compound V-6
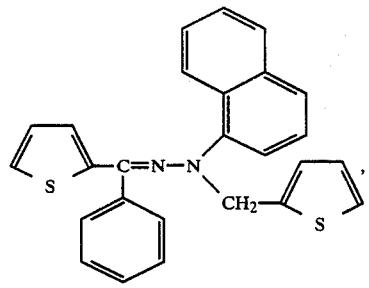
compound V-7
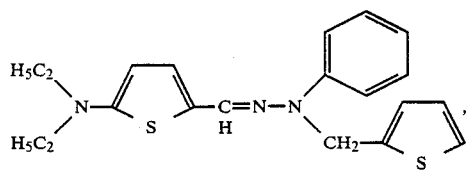
compound V-8
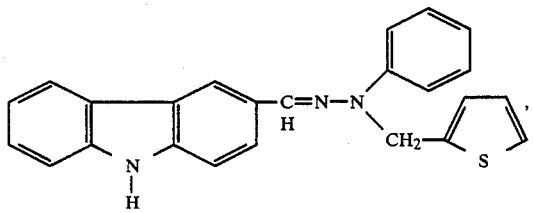
compound V-9
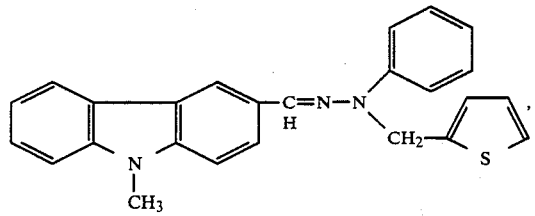
compound V-10
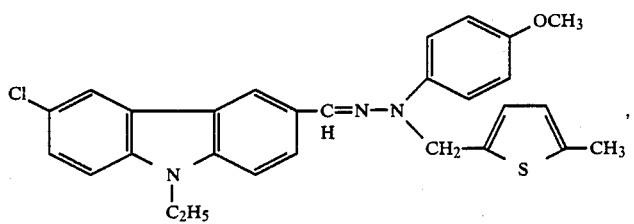
compound V-11
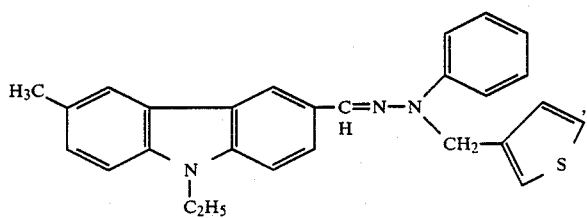
compound V-12 compound V-13
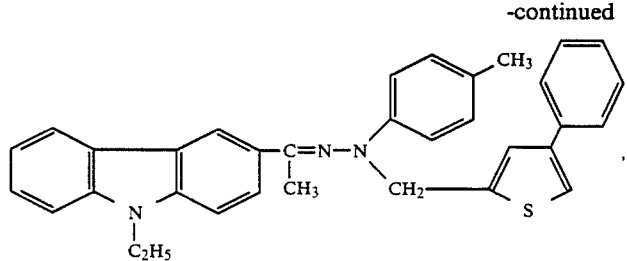
compound V-14
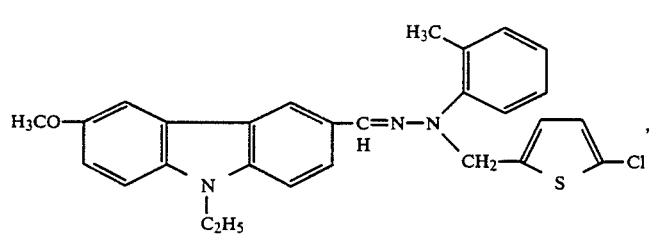
compound V-15
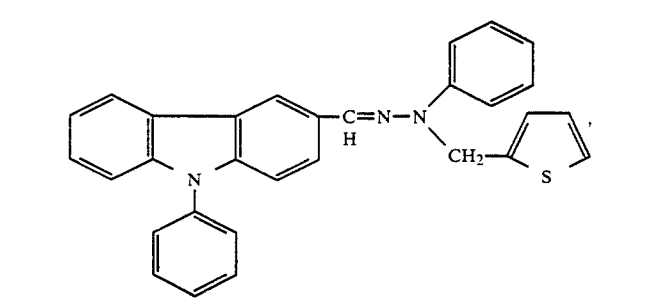
compound V-16
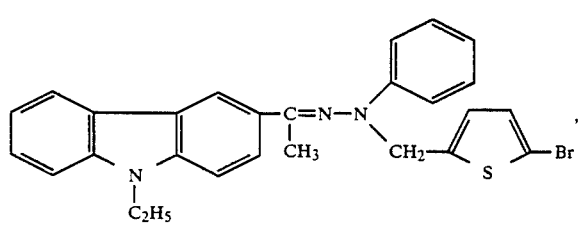
compound V-17
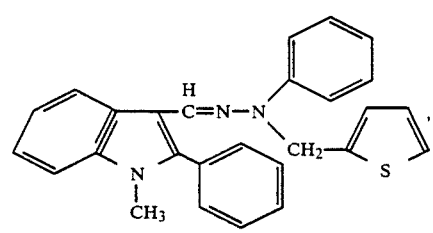
compound V-18
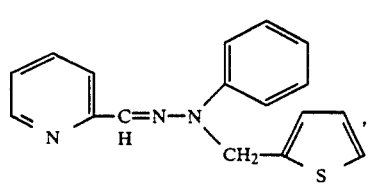
compound V-19
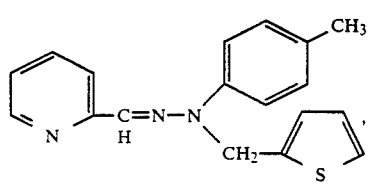

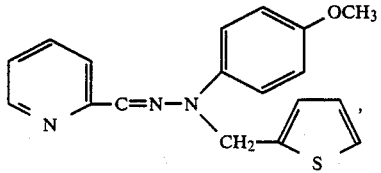

compound V-20

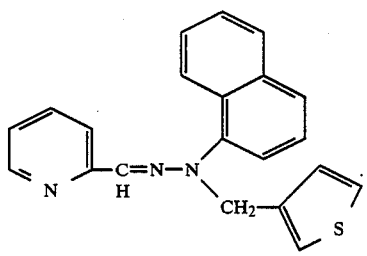

compound V-21

Examples of a photosensitive member, in which a chemical compound represented by general formula (V) is used as a charge transporting substance, will be explained.

EXAMPLE V-1

A photosensitive member having the structure shown in FIG. 1 and comprising a photosensitive layer having a thickness of 15 μm was produced in substantially the same manner as in Example I-1 except that hydrazone compound No. V-1 mentioned above was used instead of compound No. I-1.

EXAMPLE V-2

A photosensitive member having a structure corresponding to that of FIG. 3 but having no covering layer was produced in substantially the same manner as in Example I-2 except that hydrazone compound No. V-2 was used instead of compound No. I-2. The thickness of the charge transporting layer of the member was 15 μm, while the thickness of the charge generating layer was 1 μm.

EXAMPLE V-3

A photosensitive member was produced by forming a photosensitive layer in substantially the same manner as in Example V-1 except that 50 parts by weight of metal-free phthalocyanine, 100 parts by weight of hydrazone compound No. V-3 mentioned above, 50 parts by weight of a polyester resin (Vylon 200), and 50 parts by weight of PMMA were used to replace therewith the composition of the photosensitive layer of Example V-1.

EXAMPLE V-4

A photosensitive member was produced by forming a photosensitive layer in substantially the same manner as in Example V-3 except that Chlorodiane Blue was used instead of metal-free phthalocyanine.

The four photosensitive members thus produced were examined with respect to surface potential $V_s$, residual potential $V_r$, and half decay exposure amount $E_{\frac{1}{2}}$ by using white light as well as monochromatic light (wavelength: 780 nm) in the same manner as in Examples I-1 to I-4. The results of the measurements are shown in Table 9.

TABLE 9

| Example No. | White Light $V_s$ (volts) | White Light $V_r$ (volts) | White Light $E_{\frac{1}{2}}$ (lux · sec) | Light with Wavelength of 780 nm $V_s$ (volts) | Light with Wavelength of 780 nm $V_r$ (volts) | Light with Wavelength of 780 nm $E_{\frac{1}{2}}$ (μJ/cm²) |
|---|---|---|---|---|---|---|
| V-1 | 690 | 80 | 5.3 | 680 | 70 | 4.9 |
| V-2 | 670 | 100 | 6.0 | 680 | 60 | 4.7 |
| V-3 | 650 | 100 | 5.8 | 620 | 50 | 5.0 |
| V-4 | 680 | 80 | 5.0 | — | — | — |

As can be seen in Table 9, the photosensitive members of Examples V-1, V-2, V-3 and V-4 were not substantially different therebetween in the half decay exposure amount and the residual potential, and showed good surface potential characteristics. The photosensitive members of Examples V-1, V-2 and V-3, using a phthalocyanine compound as the charge generating substance, showed also excellent electrophotographic characteristics for the light with the long wavelength of 780 nm.

EXAMPLE V-5

A photosensitive member with the structure shown in FIG. 2 was produced by forming a charge generating layer and a charge transporting layer with a dry thickness of 20 μm in substantially the same manner as in Example I-5 except that hydrazone compound No. V-4 was used instead of compound No. I-4. This photosensitive member was charged by corona discharge at −6.0 kV for 0.2 second and examined with respect to electrophotographic characteristics. Good results were obtained, namely $V_s = -700$ V, $V_r = -60$ V and $E_{\frac{1}{2}} = 4.3$ lux·sec.

EXAMPLE V-6

A charge generating layer with a thickness of about 1 μm was formed on an aluminum support in the same manner as in Example I-6. A charge transporting layer with a thickness of about 15 μm was formed on the charge generating layer in substantially the same manner as in Example I-6 except that hydrazone compound No. V-5 was used instead of compound No. I-5.

The photosensitive member thus obtained was charged by corona discharge at −6.0 kV for 0.2 second and examined with respect to electrophotographic characteristics in the same manner as in Example V-5.

Good results were obtained, namely $V_s = -700$ V and $E_{\frac{1}{2}} = 5.0$ lux·sec.

EXAMPLE V-7

Photosensitive members were produced by forming respective photosensitive layers in substantially the same manner as in Example V-4 except that the compounds Nos. V-6 to V-21 were respectively used instead of compound No. V-3, and were examined with respect to half decay exposure amount by using the electrostatic recording paper testing apparatus Model SP-428. The results are shown in Table 10, in which the half decay exposure amounts $E_{\frac{1}{2}}$ (lux·sec) are values measured under the experimental conditions where the members were positively charged in the dark by corona discharge at +6.0 kV for 10 seconds and irradiated with white light at an illuminance of 2 luxes.

TABLE 10

| Compound No. | $E_{\frac{1}{2}}$(lux · sec) |
|---|---|
| V-6 | 6.1 |
| V-7 | 5.5 |
| V-8 | 6.0 |
| V-9 | 5.2 |
| V-10 | 5.9 |
| V-11 | 5.8 |
| V-12 | 5.4 |
| V-13 | 6.3 |
| V-14 | 5.4 |
| V-15 | 5.8 |
| V-16 | 5.1 |
| V-17 | 4.9 |
| V-18 | 6.3 |
| V-19 | 5.7 |
| V-20 | 5.5 |
| V-21 | 6.0 |

As can be seen in Table 10, the photosensitive members using the respective hydrazone compounds Nos. V-6 to V-21 were satisfactory with respect to the half decay exposure amount $E_{\frac{1}{2}}$, namely sensitivity.

A description will now be made of a hydrazone compound prepared by condensing a carbonyl compound of the formula:

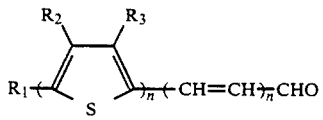

with a hydrazine compound of the formula:

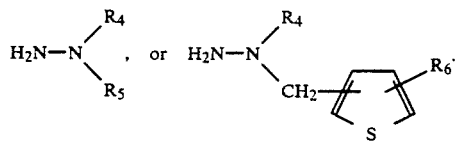

The carbonyl compound is condensed with a hydrazine compound in an alcohol such as ethanol in the presence of a small amount of a catalyst such as hydrochloric acid if necessary evolving water, according to the following reaction formula:

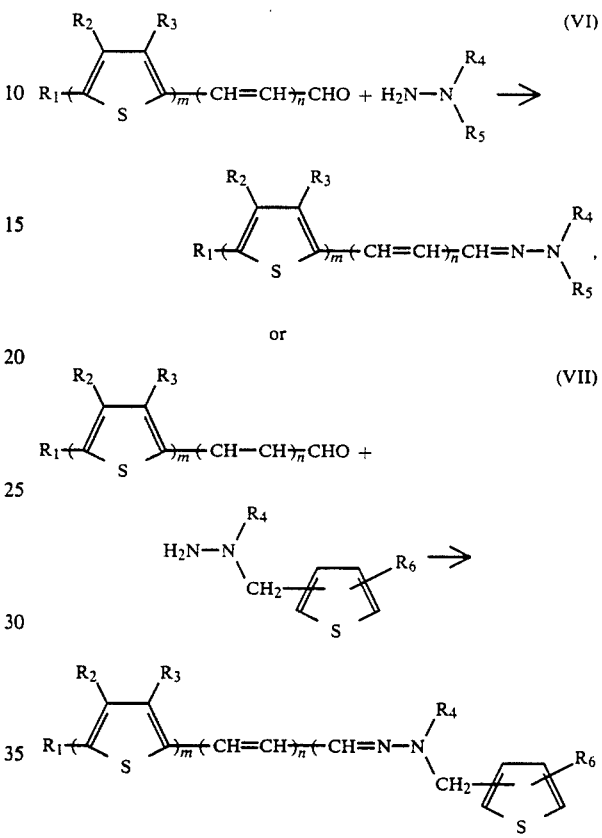

to synthesize a hydrazone compound of the above-mentioned general formula (VI) or (VII). In general formulae (VI) and (VII), each of $R_1$, $R_2$, $R_3$ and $R_6$ stands for a hydrogen atom, a halogen atom, an alkyl group, a alkoxy group, a hydroxy group, an allyl group, a nitro group, an aryl group which may have at least one substituent, or an amino group; each of $R_4$ and $R_5$ stands for an aryl group which may have at least one substituent; n stands for an integer of 1 or 2; and m stands for an integer of 2 to 5.

Specific examples of hydrazone compounds of general formula (VI) or (VII) prepared in the above-mentioned manner include:

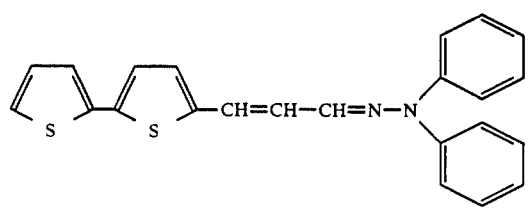

compound VI-1

-continued
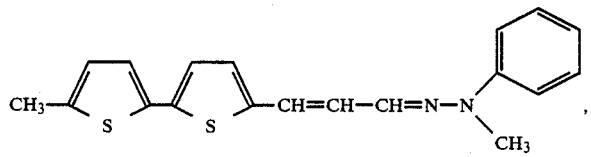
compound VI-2
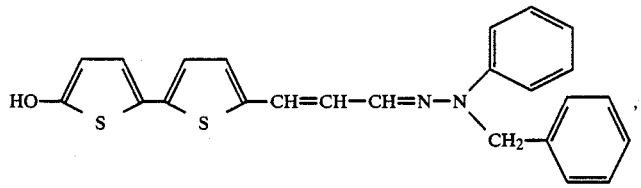
compound VI-3
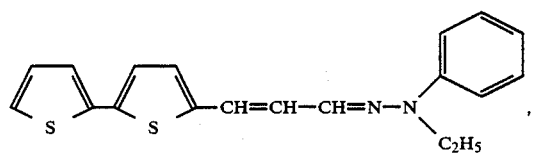
compound VI-4
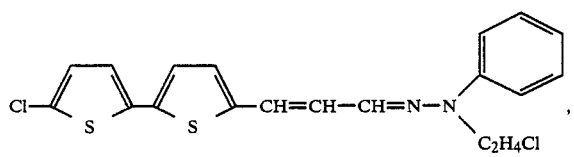
compound VI-5
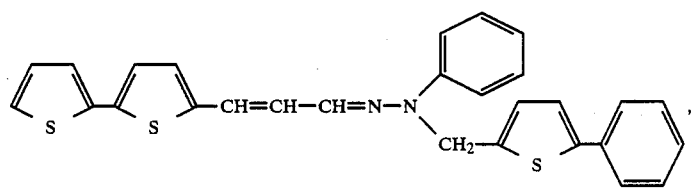
compound VI-6
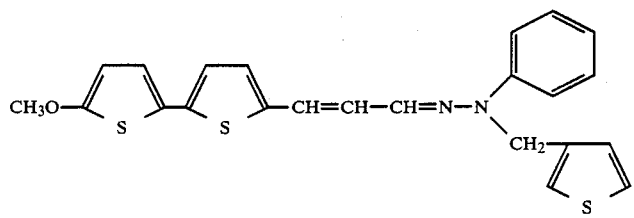
compound VI-7
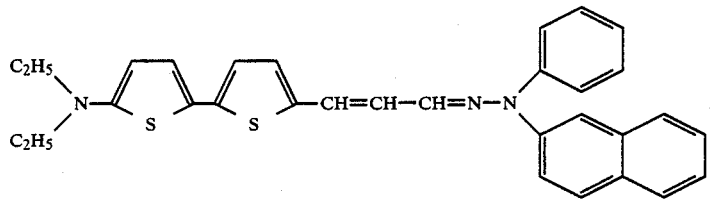
compound VI-8
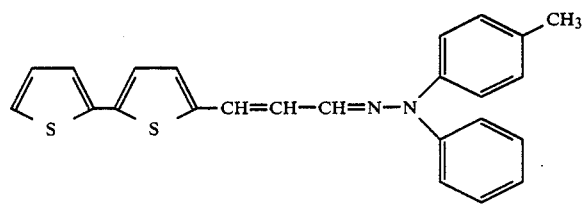
compound VI-9

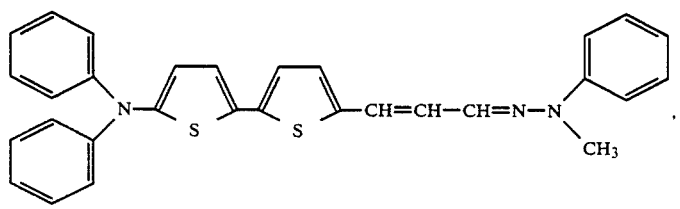
compound VI-10
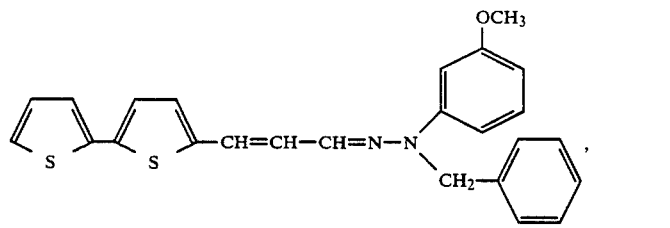
compound VI-11
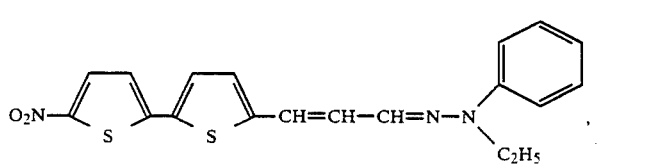
compound VI-12
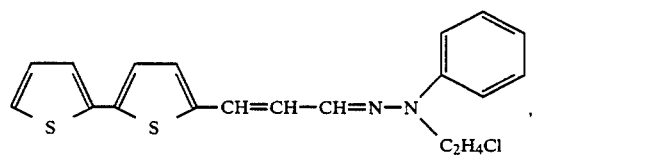
compound VI-13
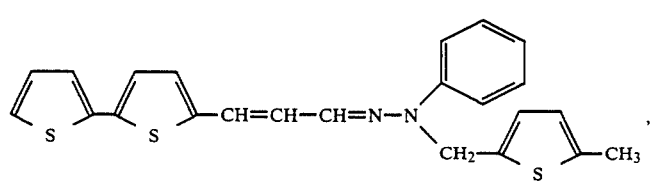
compound VI-14
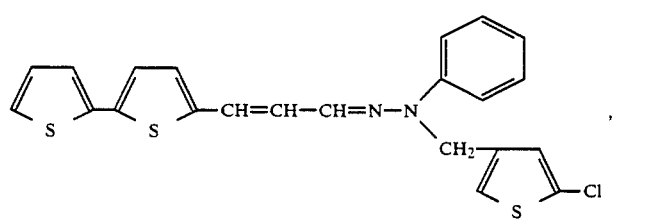
compound VI-15
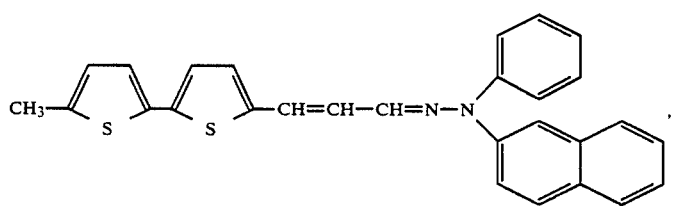
compound VI-16
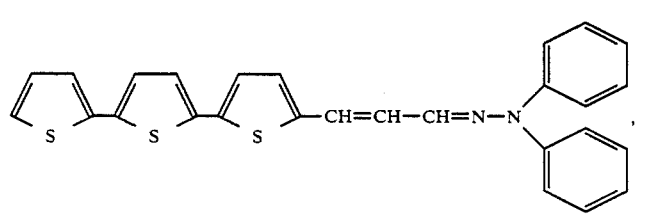
compound VI-17

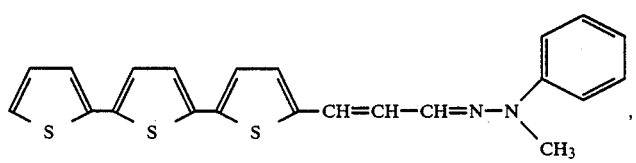
compound VI-18
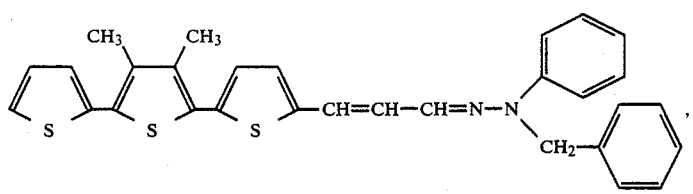
compound VI-19
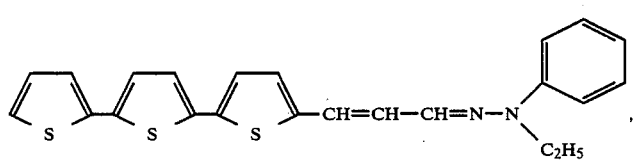
compound VI-20
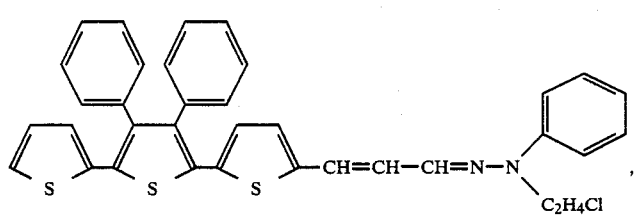
compound VI-21
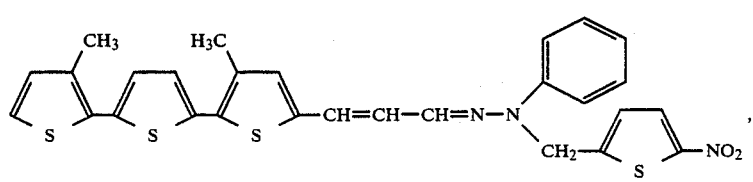
compound VI-22
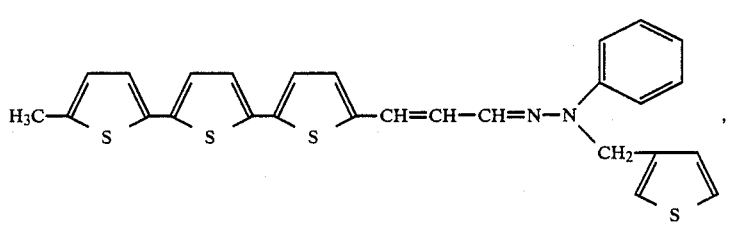
compound VI-23
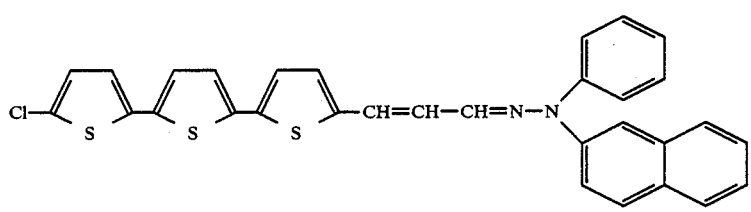
compound VI-24
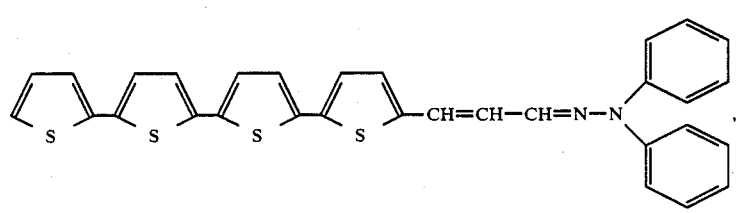
compound VI-25 compound VI-26
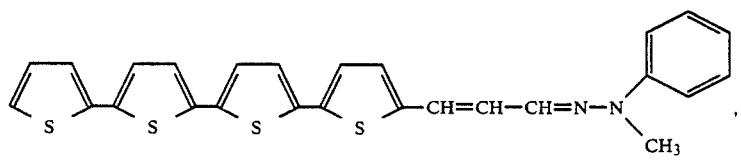
compound VI-27
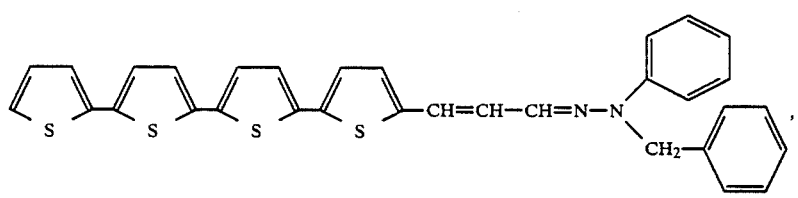
compound VI-28
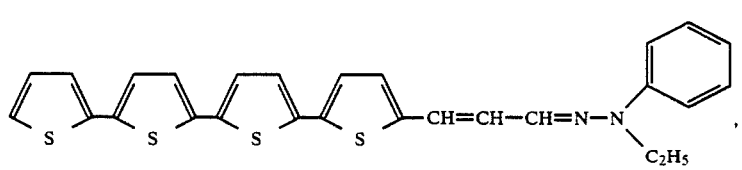
compound VI-29
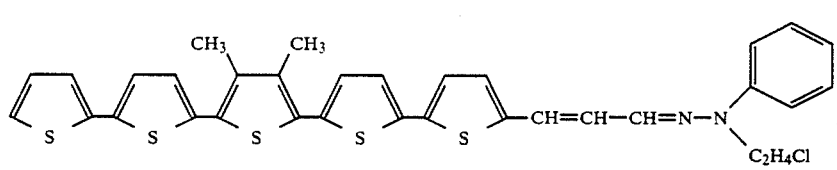
compound VI-30
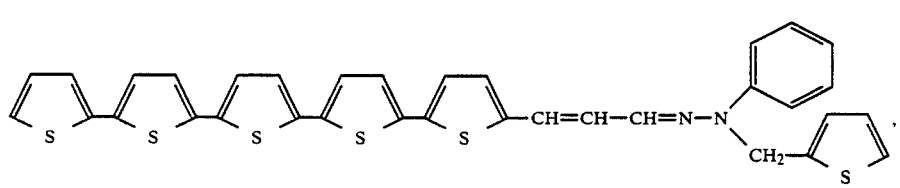
compound VI-31
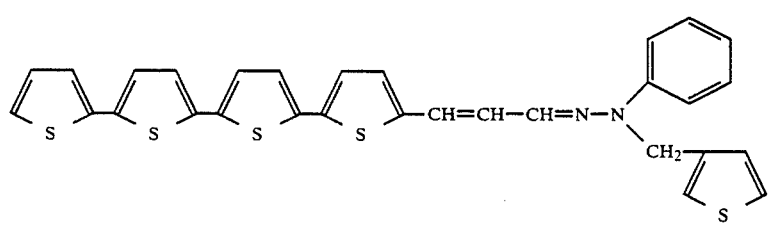
compound VI-32
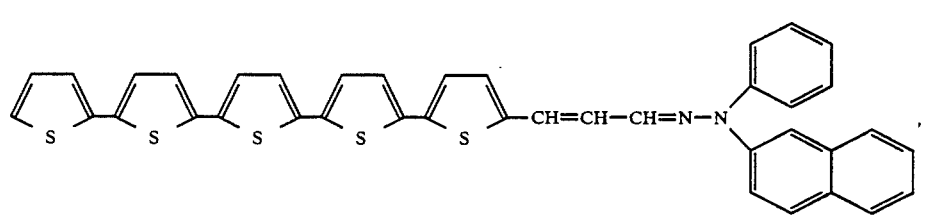
compound VI-33
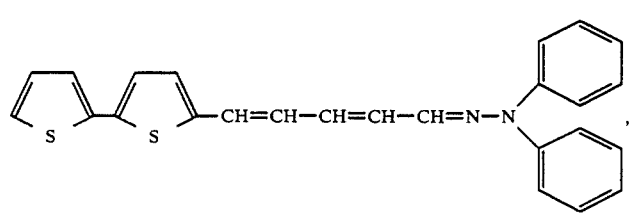

-continued

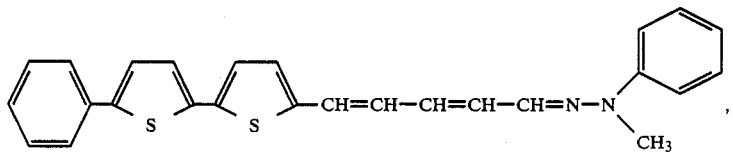

compound VI-34

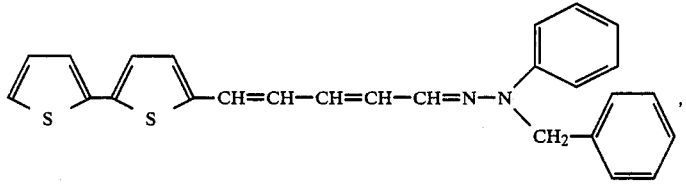

compound VI-35

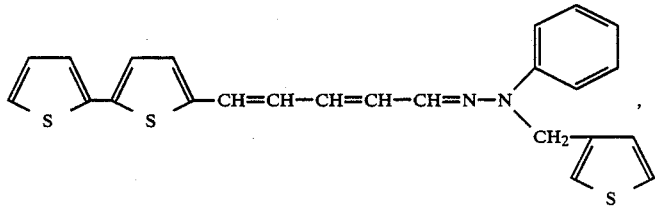

compound VI-36

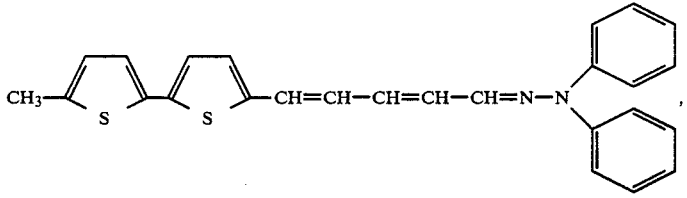

compound VI-37

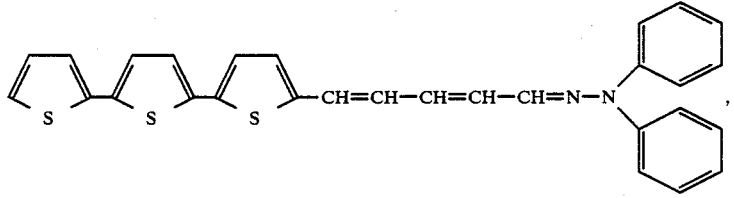

compound VI-38

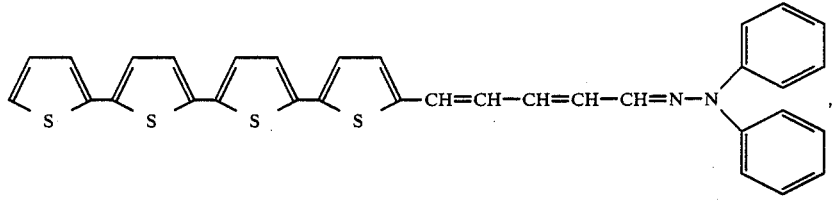

compound VI-39 and

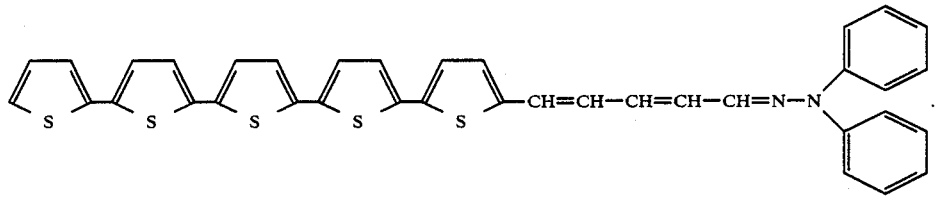

compound VI-40

Examples of the photosensitive member, in which a chemical compound represented by the general formula (VI) is used as a charge transporting substance, will be explained.

EXAMPLE VI-1

A photosensitive member having the structure shown in FIG. 1 and comprising a photosensitive layer having a thickness of 15 μm was produced in substantially the same manner as in Example I-1 except that hydrazone compound No. VI-1 mentioned above was used instead of compound No. I-1.

EXAMPLE VI-2

A photosensitive member having a structure corresponding to that of FIG. 3 was produced in substantially the same manner as in Example I-2 except that hydrazone compound No. VI-2 was used instead of compound No. I-2. The thickness of the charge transporting layer of the member was 15 μm, while the thickness of the charge generating layer was 1 μm.

EXAMPLE VI-3

A photosensitive member was produced by forming a photosensitive layer in substantially the same manner as in Example VI-1 except that 50 parts by weight of metal-free phthalocyanine, 100 parts by weight of hydrazone compound No. VI-3 mentioned above, 50 parts by weight of a polyester resin (Vylon 200), and 50 parts by weight of PMMA were used to replace therewith the composition of the photosensitive layer of Example VI-1.

EXAMPLE VI-4

A photosensitive member was produced by forming a photosensitive layer in substantially the same manner as in Example VI-3 except that Chlorodiane Blue was used instead of metal-free phthalocyanine.

The four photosensitive members thus produced were examined with respect to surface potential $V_s$, residual potential $V_r$, and half decay exposure amount $E_{\frac{1}{2}}$ by using white light as well as a monochromatic light (wavelength: 780 nm) in the same manner as in Examples I-1 to I-4. The results of the measurements are shown in Table 11.

TABLE 11

| Example No. | White Light | | | Light with Wavelength of 780 nm | | |
|---|---|---|---|---|---|---|
| | $V_s$ (volts) | $V_r$ (volts) | $E_{\frac{1}{2}}$ (lux · sec) | $V_s$ (volts) | $V_r$ (volts) | $E_{\frac{1}{2}}$ (μJ/cm$^2$) |
| VI-1 | 670 | 90 | 5.8 | 660 | 80 | 6.1 |
| VI-2 | 640 | 100 | 5.2 | 680 | 70 | 6.3 |
| VI-3 | 650 | 70 | 6.5 | 660 | 60 | 6.1 |
| VI-4 | 700 | 100 | 6.7 | — | — | — |

As can be seen in Table 11, the photosensitive members of Examples VI-1, VI-2, VI-3 and VI-4 were comparable with one another in respect of the half decay exposure amount and the residual potential, and showed good surface potential characteristics. The photosensitive members of Examples VI-1, VI-2 and VI-3, using a phthalocyanine compound as the charge generating substance, also showed the high sensitivity for light with a long wavelength of 780 nm, thus proving that they can be satisfactorily used in semiconductor laser printers.

EXAMPLE VI-5

A photosensitive member with the structure shown in FIG. 2 was produced by forming a charge generating layer and a charge transporting layer with a dry thickness of 20 μm in substantially the same manner as in Example I-5 except that hydrazone compound No. VI-4 was used instead of compound No. I-4. After this photosensitive member was charged by corona discharge at −6.0 kV for 0.2 second and examined with respect to electrophotographic characteristics. Good results were obtained, namely $V_s = -610$ V, $V_r = -60$ V and $E_{\frac{1}{2}} = 5.2$ lux·sec.

EXAMPLE VI-6

A charge generating layer with a thickness of about 1 μm was formed on an aluminum support in the same manner as in Example I-6. A charge transporting layer with a thickness of about 15 μm was formed on the charge generating layer in substantially the same manner as in Example I-6 except that hydrazone compound No. VI-5 was used instead of compound No. I-5.

The photosensitive member thus obtained was charged by corona discharge at −6.0 kV for 0.2 second and examined with respect to electrophotographic characteristics in the same manner as in Example VI-5. Good results were obtained, namely $V_s = -630$ V and $E_{\frac{1}{2}} = 6.4$ lux·sec.

EXAMPLE VI-7

Photosensitive members were produced by forming respective photosensitive layers in substantially the same manner as in Example VI-4 except the compounds Nos. VI-6 to VI-40 were respectively used instead of compound No. VI-3, and were examined with respect to half decay exposure amount by using the electrostatic recording paper testing apparatus Model SP-428. The results are shown in Table 12, in which the half decay exposure amounts $E_{\frac{1}{2}}$ (lux·sec) are values obtained under the experimental conditions where the members were positively charged in the dark by corona discharge at +6.0 kV for 10 seconds and irradiated with white light at an illuminance of 2 luxes.

TABLE 12

| Compound No. | $E_{\frac{1}{2}}$ (lux · sec) |
|---|---|
| VI-6 | 5.3 |
| VI-7 | 6.8 |
| VI-8 | 7.1 |
| VI-9 | 6.6 |
| VI-10 | 7.6 |
| VI-11 | 8.1 |
| VI-12 | 6.2 |
| VI-13 | 4.9 |
| VI-14 | 5.2 |
| VI-15 | 5.9 |
| VI-16 | 6.9 |
| VI-17 | 7.7 |
| VI-18 | 6.6 |
| VI-19 | 5.9 |
| VI-20 | 6.1 |
| VI-21 | 5.9 |
| VI-22 | 4.2 |
| VI-23 | 6.9 |
| VI-24 | 5.9 |
| VI-25 | 6.6 |
| VI-26 | 6.9 |
| VI-27 | 5.1 |
| VI-28 | 4.6 |
| VI-29 | 7.1 |
| VI-30 | 5.8 |
| VI-31 | 6.2 |
| VI-32 | 6.2 |
| VI-33 | 4.8 |
| VI-34 | 6.1 |
| VI-35 | 7.8 |
| VI-36 | 7.8 |
| VI-37 | 5.9 |
| VI-38 | 5.2 |
| VI-39 | 5.8 |
| VI-40 | 6.1 |

As can be seen in Table 12, the photosensitive members using the respective hydrazone compounds Nos.

VI-6 to VI-40 as the charge transporting substance were satisfactory with respect to the half decay exposure amount $E_{\frac{1}{2}}$.

According to the present invention, hydrazone compound represented by any one of the aforementioned chemical formulae is used as a charge transporting substance in a photosensitive layer formed on an electroconductive substrate, resulting in a photosensitive member showing high sensitivity and excellent characteristics in repeated use when adapted to either a positive charge mode or a negative charge mode. A suitable charge generating substance can be chosen so as to be adapted to the kind of exposure light source. By way of example, a phthalocyanine compound or a bisazo compound can be used as a charge generating substance to provide a photosensitive member capable of being used in semiconductor laser printers. If necessary, a covering layer may be provided on the surface of a photosensitive member to improve the durability thereof.

The invention has been described in detail with respect to preferred embodiments, and it will now be apparent from the foregoing to those skilled in the art that changes and modifications may be made without departing from the invention in its broader aspects, and it is the invention, therefore, in the appended claims to cover all such changes and modifications as fall within the true spirit of the invention.

What is claimed is:

1. A photosensitive member for electrophotography comprising:
    a substrate; and
    a photosensitive layer formed on said substrate and including a charge generating substance and at least one hydrazone compound as a charge transporting substance represented by the following general formula (I):

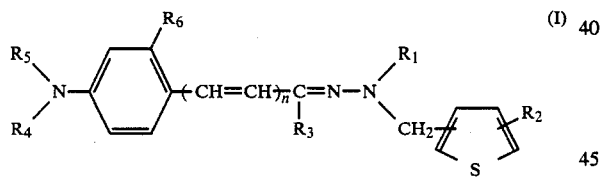

wherein $R_1$ stands for an aryl group which may have at least one substituent; each of $R_2$, $R_3$, $R_4$, $R_5$, $R_6$ stands for a hydrogen atom, a halogen atom, an alkyl group, an alkoxy group, a hydroxy group, a nitro group, an allyl group, an aryl group which may have at least one substituent, or an aralkyl group; and n stands for an integer of 0 or 1.

2. A photosensitive member as claimed in claim 1, wherein said photosensitive layer comprises a dispersion of a charge generating substance and a charge transporting substance in a binder resin, and said charge transporting substance is a compound selected from hydrazone compounds represented by the general formulae (I).

3. The photosensitive member as claimed in claim 1, wherein said photosensitive layer comprises a laminate of a charge transporting layer mainly composed of a charge transporting substance and a charge generating layer, and said charge transporting substance is a compound selected from hydrazone compounds represented by the general formulae (I).

4. A photosensitive member for electrophotography comprising:
    a substrate; and
    a photosensitive layer formed on said substrate and including a charge generating substance and at least one hydrazone compound as a charge transporting substance represented by the following general formula (II):

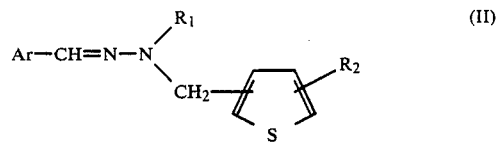

wherein $R_1$ stands for an aryl group which may have at least one substituent; $R_2$ stands for a hydrogen atom, a halogen atom, an alkyl group, an aryl group, or a nitro group; and Ar stands for a condensed-ring polycyclic aromatic hydrocarbon group.

5. A photosensitive member as claimed in claim 4, wherein said photosensitive layer comprises a dispersion of a charge generating substance and a charge transporting substance in a binder resin, and said charge transporting substance is a compound selected from hydrazone compounds represented by the general formulae (II).

6. The photosensitive member as claimed in claim 4, wherein said photosensitive layer comprises a laminate of a charge transporting layer mainly composed of a charge transporting substance and a charge generating layer, and said charge transporting substance is a compound selected from hydrazone compounds represented by the general formulae (II).

7. A photosensitive member for electrophotography comprising:
    a substrate; and
    a photosensitive layer formed on said substrate and including a charge generating substance and at least one hydrazone compound as a charge transporting substance represented by the following general formula (III):

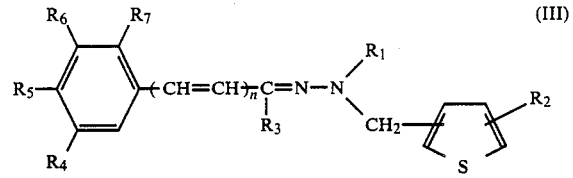

wherein $R_1$ stands for an aryl group which may have at least one substituent; each of $R_2$, $R_3$, $R_4$, $R_5$, $R_6$ and $R_7$ stands for a hydrogen atom, a halogen atom, an alkyl group, an alkoxy group, a phenoxy group, a nitro group, a hydroxy group, an aryl group or a styryl group; and n stands for an integer of 0 to 1.

8. A photosensitive member as claimed in claim 7, wherein said photosensitive layer comprises a dispersion of a charge generating substance and a charge transporting substance in a binder resin, and said charge transporting substance is a compound selected from hydrazone compounds represented by the general formulae (III).

9. The photosensitive member as claimed in claim 7, wherein said photosensitive layer comprises a laminate of a charge transporting layer mainly composed of a charge transporting substance and a charge generating layer, and said charge transporting substance is a compound selected from hydrazone compounds represented by the general formulae (III).

10. A photosensitive member for electrophotography comprising:
a substrate; and
a photosensitive layer formed on said substrate and including a charge generating substance and at least one hydrazone compound as a charge transporting substance represented by the following general formula (VI):

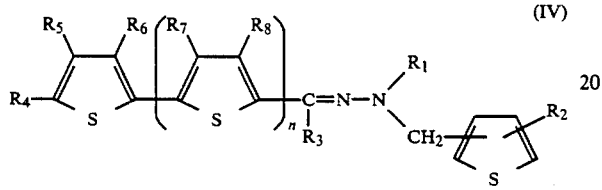
(IV)

wherein $R_1$ stands for an aryl group which may have at least one substituent; each of $R_2$, $R_3$, $R_4$, $R_5$, $R_6$, $R_7$ and $R_8$ stands for a hydrogen atom, a halogen atom, an alkoxy group, an alkyl group, a nitro group, a hydroxy group, an aryl group or an amino group which may have at least one substituent; and n stands for an integer of 1, 2, 3 or 4.

11. A photosensitive member as claimed in claim 10, wherein said photosensitive layer comprises a dispersion of a charge generating substance and a charge transporting substance in a binder resin, and said charge transporting substance is a compound selected from hydrazone compounds represented by the general formulae (IV).

12. The photosensitive member as claimed in claim 10, wherein said photosensitive layer comprises a laiminate of a charge transporting layer mainly composed of a charge transporting substance and a charge generating layer, and said charge transporting substance is a compound selected from hydrazone compounds represented by the general formulae (IV).

13. A photosensitive member for electrophotography comprising:
a substrate; and
a photosensitive layer formed on said substrate and including a charge generating substance and at least one hydrazone compound as a charge transporting substance represented by the following general formula (V):

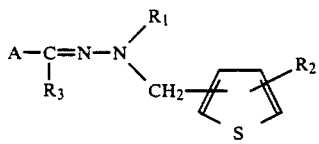
(V)

wherein $R_1$ stands for an aryl group which may have at least one substituent; each of $R_2$ and $R_3$ stands for a hydrogen atom, a halogen atom, an alkyl group, an alkoxy group, an aryl group or a nitro group; and Ar stands for a heterocyclic group which may have at least one substituent.

14. A photosensitive member as claimed in claim 13, wherein said photosensitive layer comprises a dispersion of a charge generating substance and a charge transporting substance in a binder resin, and said charge transporting substance is a compound selected from hydrazone compounds represented by the general formulae (V).

15. The photosensitive member as claimed in claim 13, wherein said photosensitive layer comprises a laminate of a charge transporting layer mainly composed of a charge transporting substance and a charge generating layer, and said charge transporting substance is a compound selected from hydrazone compounds represented by the general formulae (V).

16. A photosensitive member for electrophotography comprising:
a substrate; and
a photosensitive layer formed on said substrate and including a charge generating substance and at least one hydrazone compound as a charge transporting substance represented by the following general formula (VI) or (VII):

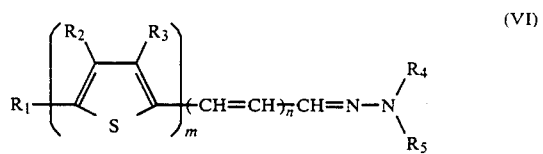
(VI)

or,

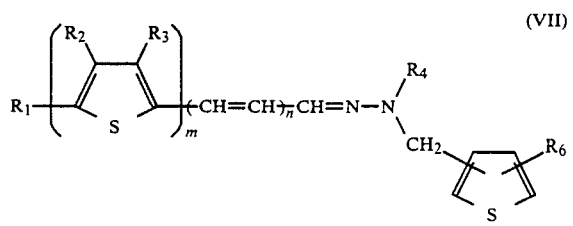
(VII)

wherein each of R1, R2, R3 and R6 stands for a hydrogen atom, a halogen atom, an alkyl group, an alkoxy group, a hydroxy group, an allyl group, a nitro group, an aryl group which may have at least one substituent, or an amine group; each of R4 and R5 stands for an aryl group which may have at least one substituent; n stands for an integer of 0 or 1; and m stands for an integer of 2 to 5.

17. A photosensitive member as claimed in claim 16, wherein said photosensitive layer comprises a dispersion of a charge generating substance and a charge transporting substance in a binder resin, and said charge transporting substance is a compound selected from hydrazone compounds represented by the general formulae (VI) or (VII).

18. The photosensitive member as claimed in claim 16, wherein said photosensitive layer comprises a laminate of a charge transporting layer mainly composed of a charge transporting substance and a charge generating layer, and said charge transporting substance is a compound selected from hydrazone compounds represented by the general formulae (VI) or (VII).

* * * * *

UNITED STATES PATENT AND TRADEMARK OFFICE
CERTIFICATE OF CORRECTION

PATENT NO. : 4,957,837
DATED : September 18th, 1990
INVENTOR(S) : Masami Kuroda et al.

It is certified that error appears in the above-identified patent and that said Letters Patent is hereby corrected as shown below:

On the title page: Item [30] Foreign Application Priority Data should read:

Oct. 15, 1987 [JP]   Japan ....... 62-260531
    Oct. 20, 1987 [JP]   Japan ....... 62-265112
    Oct. 20, 1987 [JP]   Japan ....... 62-265113
    Oct. 21, 1987 [JP]   Japan ....... 62-265751
    Oct. 21, 1987 [JP]   Japan ....... 62-265752
    Dec.  9, 1987 [JP]   Japan ....... 62-311312

Signed and Sealed this

Fourth Day of February, 1992

*Attest:*

HARRY F. MANBECK, JR.

*Attesting Officer*      *Commissioner of Patents and Trademarks*